(12) United States Patent
Benkovic et al.

(10) Patent No.: US 7,820,413 B2
(45) Date of Patent: *Oct. 26, 2010

(54) INCREMENTALLY TRUNCATED NUCLEIC ACIDS AND METHODS OF MAKING SAME

(75) Inventors: Stephen J. Benkovic, State College, PA (US); Marc Ostermeier, Baltimore, MD (US); Stefan Lutz, State College, PA (US); Andrew E. Nixon, Quincy, MA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/033,672

(22) Filed: Feb. 19, 2008

(65) Prior Publication Data

US 2008/0227659 A1     Sep. 18, 2008

Related U.S. Application Data

(63) Continuation of application No. 09/718,465, filed on Nov. 15, 2000, now Pat. No. 7,332,308.

(51) Int. Cl.
*C12N 15/64* (2006.01)
*C12N 5/00* (2006.01)
*C12Q 1/68* (2006.01)
*C40B 50/00* (2006.01)
*C40B 50/06* (2006.01)
*C07H 21/02* (2006.01)

(52) U.S. Cl. .......... 435/91.42; 435/6; 435/410; 435/DIG. 47; 536/23.1; 506/23; 506/26

(58) Field of Classification Search ............. 435/91.42, 435/6, 410, DIG. 47, 23.1; 506/23, 26
See application file for complete search history.

(56) References Cited

U.S. PATENT DOCUMENTS 7,332,308 B1 * 2/2008 Benkovic et al. ......... 435/91.42

OTHER PUBLICATIONS

Ostermeier et al (Combinatorial protein engineering by incremental truncation, PNAS, vol. 96, pp. 3562-3567, Mar. 1999).*

* cited by examiner

*Primary Examiner*—Amber D. Steele
*Assistant Examiner*—Shannon Janssen
(74) *Attorney, Agent, or Firm*—Husch Blackwell Welsh & Katz

(57) ABSTRACT

A series of methods that utilize the incremental truncation of nucleic acids are described to create a plurality of modified nucleic acids and hybrid polypeptides. A plurality of substantially all possible single base-pair deletions of a given nucleic acid sequence is created. A method of making shuffled incremental truncated nucleic acids, which is independent of nucleic acid sequence homology, is also described. These methods can be used in protein engineering, protein folding, protein evolution, and the chemical synthesis of novel hybrid proteins and polypeptides.

9 Claims, 13 Drawing Sheets

INCREMENTALLY TRUNCATED NUCLEIC ACIDS AND METHODS OF MAKING SAME

CROSS-REFERENCE TO RELATED APPLICATIONS

This application claims priority of Provisional Application No. 60/135,429 (filed May 21, 1999) and Provisional Application No. 60/172,525 (filed Dec. 17, 1999), and is a continuation-in-part of U.S. patent application Ser. No. 09/575,345 filed May 19, 2000, all of which are incorporated herein by reference.

STATEMENT OF GOVERNMENTAL RIGHTS

This invention was made with United States Government support in the form of a grant from the National Institute of Health, Grant No. GM24129 and a National Institute of Health postdoctoral fellowship Grant No. GM18560. The United States Government has certain rights in this invention.

FIELD OF THE INVENTION

The present invention is generally directed to nucleic acid and polypeptide mixtures, and more specifically to methods for incrementally truncating nucleic acids for the creation of hybrid nucleic acids and hybrid polypeptides, as well as the hybrid nucleic acids and polypeptides themselves.

BACKGROUND OF THE INVENTION

Protein mutagenesis has long been used as a tool for structure/function studies of proteins. With the advent of modern DNA manipulation techniques and advancements in protein structure determination, large numbers of protein sequences and structures are available that can be sorted into groups or superfamilies based on structural similarity. Such groupings demonstrate that proteins that are structurally similar often catalyze similar reactions and have active sites with shared amino acid residues. Further, these groupings facilitate identification of side chain residues that are important in binding and catalysis, and allow for their modification so as to yield proteins with altered properties.

Such structure-based rational approaches to protein engineering, through introduction of point mutations, exchange of secondary structural elements, and exchange of whole domains or subunits, have given rise to enzymes that have altered substrate specificities, catalytic properties and oligomeric states. Although few protein-engineering failures have been published, the difficulty in rationally engineering an enzyme to have a specific function is widely appreciated. Any alteration introduced into a wildtype protein can disrupt the fine balance that nature has achieved, often in unpredictable ways, and consequently give rise to proteins that are unstable, fail to fold properly and lack catalytic activity. As a result of the difficulties encountered using strict rational design approaches, there is an increasing trend towards the use of molecular biology strategies that mimic evolutionary processes. These strategies are known as "directed evolution."

Most directed evolution strategies incorporate some method of introducing random mutations into a gene followed by screening or selection for a desired property. The cycle is then repeated several times until the desired property is achieved or until further cycling produces no improvement in the desired property. Early methodologies utilized point mutations generated by error-prone PCR, chemical mutagenesis or mutator strains of E. coli. This type of approach is something akin to an asexual evolutionary process with non-beneficial and beneficial mutations becoming fixed. Such strategies have been particularly successful in achieving improvements in thermostability, altering substrate specificity, and improving activity in organic solvents. However, because directed evolution is a stepwise process, only relatively small steps in sequence space can occur. Thus, the utility of current directed evolution methodologies to evolve novel catalytic sites, which presumably require large excursions in sequence space, is limited.

The advent of methods for recombination, which more closely approximates the natural evolutionary process, has had an enormous impact on directed evolution. In various methods for recombination, such as DNA shuffling, parental genes are fragmented and subsequently reassembled by PCR to reconstitute the full-length genes. During this reassembly process, novel combinations of the parental genes arise along with new point mutations. This recombination or shuffling approach generates a large library of mutant genes wherein genes that exhibit a desired function can be obtained by using an appropriate selection or screening system.

Although it is true that shuffling of families of genes with DNA homology can create hybrid proteins with new properties, such molecular breeding is only feasible for genes with sufficient genetic homology and, for this reason, is unlikely to evolve entirely novel function. It is important to realize that the primary rationale for success in the shuffling of families of genes is the similarity of the three-dimensional structures of the proteins they encode, not the degree of DNA homology. Successful directed evolution on homologous families might be equally or better served by the creation of genes with crossovers between family members at regions of little or no genetic homology. However, current DNA shuffling methodologies only produce crossovers within regions of sufficient homology and within significant stretches of identity. Furthermore, crossovers are biased towards those regions of highest identity.

The increasing numbers of protein structures available and the study of enzyme structural families have shown that many proteins with little or no DNA homology can have high protein structural homology. Constructing hybrids of such structural homologues may well be an important strategy for engineering novel activities; however, no combinatorial approach for the construction of such hybrids has been reported.

Work by some of the inventors focused on the inter-conversion of formyltetrahydrofolate-utilizing enzymes. Active hybrids were created by engineering a functional hybrid enzyme through fusing domains from two enzymes, expressed on separate vectors, that overall had very little genetic homology. Discrete domain fusions were made between the glycinamide ribonucleotide (GAR) binding domain of the E. coli purN gene (GAR transformylase) and the formyl-tetrahydrofolate binding and catalytic domain of the E. coli purU gene (formyltetrahydro-folate hydrolase). Although a hybrid enzyme was created that had the desired property (GAR transformylase activity), this activity was low. Ostermeier, Nixon, Shim, and Benkovic, *Proc. Natl. Acad. Sci., USA*, 96: 3562-3567 (1999), incorporated herein by reference in its entirety.

There is therefore a need for a method of making hybrid genes without regard to sequence homology. There is a demand for simple, straightforward generation of single-base truncations of nucleic acids. There is also demand for a controllable method for creating hybrid genes that span most, if not all possible truncated portions. There is also a great demand for using such hybrid gene formation to develop new methods of creating novel hybrid proteins with modified characteristics or functionalities.

The present invention provides such methods. The present invention permits the creation of nucleic acid hybrids without regard for sequence homology. The present invention also provides a straightforward, controllable method of creating individual and pluralities of hybrid truncated nucleic acids, and concomitant individual and pluralities of hybrid polypeptides, in which the hybrids cover most, if not substantially all, possible combinations of bases.

Still further benefits and advantages will be apparent to the skilled worker from the disclosures that follow.

BRIEF SUMMARY OF THE INVENTION

The present invention is directed to a method of making incremental truncation modified nucleic acids. The incremental truncation modified nucleic acids can be expressed, or can be joined to other nucleic acid sequences, such as stop codons, inteins, recombination-prone sites, dimerization domains, and/or other incremental truncation modified nucleic acids to yield nucleic acid sequences that encode novel hybrid polypeptides.

In one aspect, the present invention is directed to a method of making a plurality of expression products of an incrementally truncated nucleic acid comprising the following steps. First, a parent nucleic acid is provided. Nucleotides are then serially removed from one or both termini of the parent nucleic acid to form truncated parent nucleic acids whose length decreases incrementally over time. The serial nucleotide removal is stopped at a plurality of different times to form a plurality of incrementally truncated nucleic acids. The plurality of incrementally truncated nucleic acids is then expressed in a suitable host to form a plurality of truncated nucleic acid expression products.

The present invention is further directed to an individual incrementally truncated nucleic acid made by the above process. The present invention is still further directed to an individual truncated nucleic acid expression product made by the above process.

In another aspect, the present invention is directed to a method of making a plurality of incrementally truncated hybrid nucleic acids comprising the following steps. First, a first and second parent nucleic acid is provided. Nucleotides are then serially removed from one or both termini of the first and second parent nucleic acids to form truncated first and second parent nucleic acids whose length decreases incrementally over time. The serial nucleotide removal is stopped at a plurality of different times to form a plurality of incrementally truncated first and second nucleic acids. Then, separate incrementally truncated first nucleic acids are linked to separate incrementally truncated second nucleic acids to form a plurality of incrementally truncated hybrid nucleic acids.

The order in which the incrementally truncated first nucleic acids are linked to the incrementally truncated second nucleic acids can be altered. Thus, for example, the incrementally truncated first nucleic acid can be linked so that it encodes the N-terminal portion of the incrementally truncated hybrid nucleic acid expression product. In this case, the incrementally truncated second nucleic acid encodes the C-terminal portion of the expression product. The incrementally truncated hybrid nucleic acid thus formed is referred to herein as a first variant incrementally truncated hybrid nucleic acid.

Alternatively, the incrementally truncated second nucleic acid can be linked so that it encodes the N-terminal portion of the incrementally truncated hybrid nucleic acid expression product. In this alternative, the incrementally truncated first nucleic acid encodes the C-terminal portion of the expression product. The incrementally truncated hybrid nucleic acid thus formed is referred to herein as a second variant incrementally truncated hybrid nucleic acid.

The present invention is further directed to a method of making a plurality of transformed incrementally truncated hybrid nucleic acids comprising the step of transforming the plurality of incrementally truncated hybrid nucleic acids into a plurality of hosts to form a plurality of transformed incrementally truncated hybrid nucleic acids. The present invention is further directed to an individual incrementally truncated hybrid nucleic acid made by the above process. The present invention is still further directed to an individual transformed incrementally truncated hybrid nucleic acid made by the above process.

In yet another aspect, the present invention is directed to a method of making a plurality of shuffled incrementally truncated nucleic acids comprising the following steps. First, isolated nucleic acid inserts of a plurality of incremental truncation modified nucleic acids are provided. The isolated nucleic acid inserts are recombed for a time period and under conditions suitable to form a plurality of shuffled incrementally truncated nucleic acids.

In a preferred embodiment, the recombining comprises mixing the isolated nucleic acid inserts with a nucleic acid fragmenting enzyme for a time period and under conditions suitable to form a mixture of nucleic acid fragments of the plurality of incremental truncation modified genes. The nucleic acid fragments of the mixture are then joined with a nucleic acid ligating enzyme.

Preferably, the nucleic acid fragmenting enzyme is an endonuclease. A preferred endonuclease is DNase. The DNase is preferably DNase I. Preferably, the nucleic acid ligating enzyme is a ligase. A preferred ligase is DNA ligase.

The present invention is further directed to a method of making a plurality of transformed shuffled incrementally truncated nucleic acids comprising the step of transforming the plurality of shuffled incrementally truncated nucleic acids into a plurality of hosts to make a plurality of transformed shuffled incrementally truncated nucleic acids. The present invention is still further directed to an individual shuffled incrementally truncated nucleic acid made according to the above process. The present invention is still further directed to an individual transformed shuffled incrementally truncated nucleic acid made according to the above process.

In a still further aspect, the present invention is directed to a method of making a plurality of analog-containing incrementally truncated nucleic acids comprising the following steps. First, a plurality of nucleotide analog-containing parent nucleic acids is provided. Nucleotides are then removed from the plurality of nucleotide analog-containing parent nucleic acids with a nuclease enzyme that does not depolymerize nucleotide analogs incorporated into a nucleic acid under conditions and for a time period sufficient to form a plurality of analog-containing truncated nucleic acids.

Preferably, the plurality of nucleotide analog-containing parent nucleic acids is a plurality of nucleotide analog-containing incremental truncation modified nucleic acids. A preferred plurality of nucleotide analog-containing incremental truncation modified nucleic acids is a plurality of nucleotide analog-containing shuffled incrementally truncated hybrid nucleic acids.

Preferably, the nuclease enzyme that does not depolymerize incorporated nucleotide analogs is an exonuclease. A preferred exonuclease is exonuclease III. Preferably, the nucleotide analog is a phosphorothioate-containing nucleotide.

The present invention is further directed to a method of making a plurality of transformed nucleotide analog-containing truncated nucleic acids comprising the step of transforming the plurality of nucleotide analog-containing truncated nucleic acids into a plurality of hosts to form a plurality of transformed nucleotide analog-containing truncated nucleic acids.

In yet a further aspect, the present invention is directed to a method of creating a circular permutation incremental truncation hybrid nucleic acid comprising the following steps. First and second nucleic acids are provided. A plurality of circularly permuted nucleic acid fragments containing a randomly located restriction enzyme site is inserted between the first and second nucleic acids to form a plurality of circular permutation hybrids. The plurality of circular permutation hybrids is reacted with a restriction enzyme that recognizes and specifically hydrolyzes the randomly located restriction enzyme site for a time period and under conditions sufficient to form a plurality of circular permutation incremental truncation substrates. Nucleotides are then removed from both ends of the restriction enzyme site to form a plurality of circular permutation incrementally truncated hybrid nucleic acids. The nucleotide removal is stopped to form a plurality of circular permutation incrementally truncated hybrid nucleic acids having a gap. The gap is then closed to form a plurality of circular permutation incremental truncation hybrid nucleic acids.

The present invention is further directed to a method of making a plurality of transformed circular permutation incremental truncation hybrid nucleic acids comprising the step of transforming the plurality of circular permutation incremental truncation hybrid nucleic acids into a plurality of hosts to form a plurality of transformed circular permutation incremental truncation hybrid nucleic acids.

As used herein, the phrase "incremental truncation modified nucleic acids" refers to incrementally truncated nucleic acids, incrementally truncated hybrid nucleic acids, shuffled incrementally truncated nucleic acids, nucleotide analog-containing incrementally truncated nucleic acids, and circular permutation incremental truncation hybrid nucleic acids.

In a still further aspect, the present invention is directed to a plurality of expressed truncated parent nucleic acid products.

In another aspect, the present invention is directed to a plurality of incrementally truncated hybrid nucleic acids.

In a further aspect, the present invention is directed to a plurality of first variant incrementally truncated hybrid nucleic acids.

In a still further aspect, the present invention is directed to a plurality of second variant incrementally truncated hybrid nucleic acids.

In yet another aspect, the present invention is directed to a plurality of shuffled incrementally truncated nucleic acids.

In a further aspect, the present invention is directed to a plurality of analog-containing incrementally truncated nucleic acids.

In a still further aspect, the present invention is directed to a plurality of circularly permuted incrementally truncated hybrid nucleic acids.

BRIEF DESCRIPTION OF THE DRAWINGS

In the drawings forming a portion of this disclosure:

FIGS. 7A-7G show the construction of ITCHY libraries between two individual genes or gene fragments located on a single plasmid by simultaneous incremental truncation using nucleotide analogs by a method called THIO-ITCHY;

FIG. 9A is a description of a vector (pDIM-N5) for creating CP-ITCHY libraries, as well as includes the following DNA sequences: SEQ ID NO:6 aaggagacagtccatatg, SEQ ID NO:7 ggatccgatatcagatct and SEQ ID NO:8 actagtgct; FIG. 9B is an example of a CP insert and construction of a CP-ITCHY library;

DETAILED DESCRIPTION OF THE INVENTION

Figure 1:
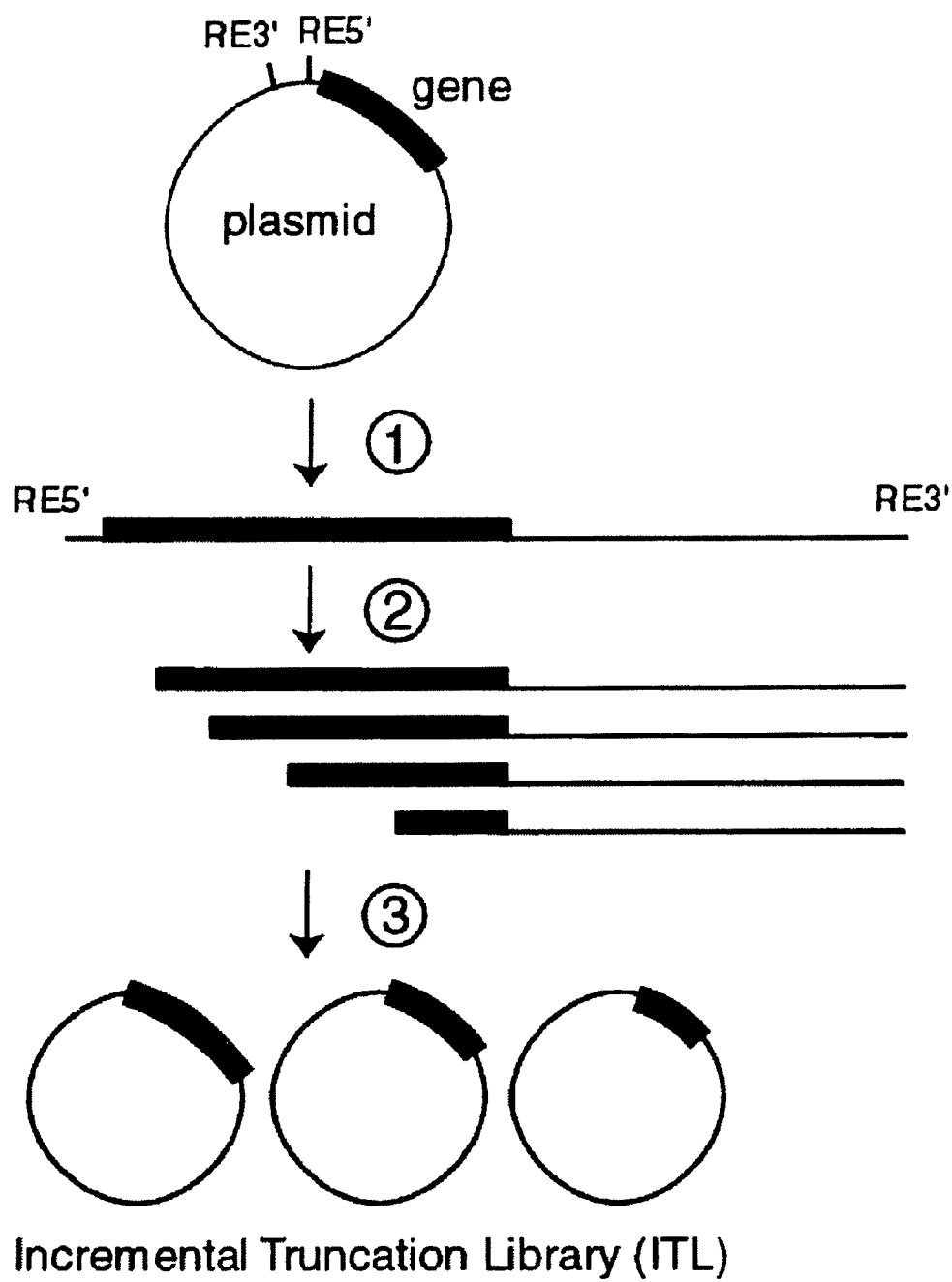
FIG. 1 schematically demonstrates the creation of an incremental truncation library.

Through the methods of the present invention, fusions of substantially all different combinations of lengths of two nucleic acids such as genes, gene fragments, PCR products, mRNAs, or cDNAs can be created. It is to be understood, however, that these biological systems cannot insure that all combinations of the various lengths of nucleic acids of interest will always be created. Nevertheless, because of the number of different hybrids that can be created according to the methods of the present invention, a great majority of the theoretical fusions can be created.

Importantly, one aspect of the invention involves various methods that circumvent homology limitations of methods of nucleic acid recombination by rearranging nucleic acids independent of their sequence homology. These rearranged nucleic acid sequences, sometimes referred to herein as hybrid nucleic acids, can encode hybrid polypeptides that have novel functional or catalytic properties. Of course, the present invention is also useful for creating hybrid polypeptides from nucleic acids with high degrees of sequence homology. The present invention, because it is independent of nucleic acid sequence homology, is applicable to potentially any desired gene, gene fragment, PCR product, and the like for the creation of hybrid polypeptides.

In one aspect, the present invention contemplates a method of making a plurality of expression products of an incrementally truncated parent nucleic acid comprising the following steps. A parent nucleic acid is first provided. Nucleotides are serially removed from one or both termini of the nucleic acid to form truncated parent nucleic acids whose length decreases incrementally over time. The serial nucleotide removal is then stopped at a plurality of different times to form a plurality of incrementally truncated nucleic acids. The plurality of incrementally truncated parent nucleic acids is expressed to form a plurality of expressed truncated parent nucleic acids.

As provided in various embodiments of the present invention, the parent nucleic acid can be selected from the group consisting of a gene, a portion of a gene, a gene fragment, a PCR product, an mRNA, a cDNA, and/or a mutant of a gene. It is to be understood that the nucleic acid can be composed of DNA or RNA. Moreover, the nucleic acid can be either single stranded or double stranded. Furthermore, it is not necessary that the nucleic acid be derived from the coding region of a gene, although in some embodiments of the invention, the nucleic acid is illustratively the coding region of a gene.

Moreover, the parent nucleic acid of various embodiments of the present invention can be a plurality or library of nucleic acids, such as a plurality or library of genes, gene portions, gene fragments, PCR products, mRNAs, cDNAs, or gene mutants.

In certain embodiments of the invention, it is preferable that the serial removal of nucleotides from a particular parent nucleic acid to form a particular modified or truncated nucleic acid have an interval of truncation lasting for about 1 to about 480 seconds, but preferably lasting less than 240 seconds, even more preferably less than 120 seconds, yet even more preferably less than 60 seconds, and most preferably the interval of truncation lasts 30 seconds.

It is also preferable, in certain embodiments of the invention, that the modified nucleic acid be formed by incremental truncation of the parent nucleic acid under conditions suitable to ensure reduction of nucleotides at a predetermined rate. It is preferable that this predetermined rate be less than about 50 nucleotides per minute and even more preferably less than about 10 nucleotides per minute. "Progressive truncation" or "serial nucleotide removal" of the parent nucleic acid includes the activity of subsequent removal of nucleotides during the truncation process.

It is preferred in the truncation step of certain embodiments of the invention that the serial reduction of nucleotides occurs in a progressive and controlled manner, that is, to ensure that relatively small groups of nucleotides are removed during the truncation process.

Incremental truncation can proceed on one or both termini of a given nucleic acid. Thus, for a given linear nucleic acid, one or both termini can be suitable substrates for the particular enzyme used to remove nucleotides from the parent nucleic acid. Thus, for example, if the particular enzyme is exonuclease III (Exo III), nucleotides are removed from the 3'-hydroxyl termini of duplex DNA only if the duplex DNA has blunt ends or a 5'-overhang. Generally, duplex DNA with a short (1-3 nucleotide) 3'-overhang is a weaker substrate for this enzyme. Generally, duplex DNA with a 3'-overhang longer than about 3 nucleotides is a poor or unacceptable substrate for this enzyme.

Other enzymes are known that can utilize different nucleic acid substrates, such as single stranded or double stranded nucleic acid, RNA or DNA, 5'-overhangs, 3'-overhangs, blunt ends, and combinations thereof. Exemplary enzymes include exonuclease III, DNase I, nuclease BAL-31, S1 nuclease, mung bean nuclease, and ribonuclease H.

Incremental truncation by the process of controlled digestion of nucleic acids is utilized for the ultimate creation of novel fusion polypeptides. For example, during this digestion in some methods of the invention, small aliquots are frequently removed and the digestion quenched. Thus by taking a plurality of samples over a plurality of different times, a plurality of truncated nucleic acids is formed that preferably contains most, if not substantially all possible single nucleotide or base pair deletions of a given piece of nucleic acid. These incremental truncation modified nucleic acids are then used to code for novel fusion polypeptides.

For the average size gene, the separate construction of all possible one-nucleotide truncations would require the assembly of hundreds of plasmids, a labor intensive and time consuming task. The present invention permits the construction of a plurality of incremental truncation modified nucleic acids containing most, if not substantially all possible truncations of a gene, gene fragment, a portion of a gene of interest, a PCR product, an mRNA, a cDNA, a mutant of said gene of interest, and the like in a single experiment as depicted in FIG. 1.

FIG. 1 shows the generalized procedure for incremental truncation. In one embodiment of the invention, incremental truncation is performed on exonuclease-susceptible DNA such as linear DNA containing a gene that has one end (terminus) protected from digestion and the other end (terminus) susceptible to digestion. In other embodiments of the invention, incremental truncation by serial removal of nucleotides from a nucleic acid proceeds from both ends (termini) of the nucleic acid. As discussed elsewhere herein, serial removal of nucleotides from the terminus of a nucleic acid depends primarily upon whether a particular terminus is an appropriate substrate for the nuclease enzyme that serially removes the nucleotides.

Workers in the art will appreciate that many of the techniques involved in the present invention make use of recombinant nucleic acid technology, using cloning vehicles and other tools of genetic engineering in the process of making the constructs of the present invention. Many of these basic techniques are described in Maniatis, Fritsch and Sambrook in *Molecular Cloning: A Laboratory Manual*; Cold Spring Harbor Laboratory: Cold Spring Harbor, N.Y., 1982, which is hereby incorporated by reference in its entirety.

Referring now to FIG. 1, serial removal of nucleotides from one gene terminus is accomplished, for example, by (as shown in step 1) digestion of plasmid DNA with two restriction enzymes. A first restriction enzyme produces a 3' overhang (RE3'; that is resistant to Exo III digestion) and a second restriction enzyme produces a 5' overhang (RE5'; that is susceptible to Exo III digestion, i.e., is an appropriate substrate for Exo III).

Step 2 illustrates one embodiment in which the digestion with exonuclease III proceeds under conditions such that the digestion rate is slow enough that the removal of aliquots at frequent intervals results in a plurality of incrementally truncated parent nucleic acids with sequential, one-nucleotide deletions.

In step 3, the ends of the DNA are blunted by treatment with a single stranded nuclease (such as S1 nuclease or mung bean nuclease) and the Klenow fragment so that unimolecular ligation results in the desired plurality of incrementally truncated genes. For some applications, additional DNA manipulations are required before recircularizing the vector.

Any enzyme that can digest nucleic acids in a controllable, directional manner can be utilized in the methodologies described herein. In the following examples, Exo III has been used and exhibits the desired properties. Exo III has been previously shown to be useful in the creation of large truncations of linear DNA and for techniques in the sequencing of large genes. However, previous techniques utilized the digestion rate of Exo III at 37° C. (approximately 500 bases per minute), which is much too fast for some embodiments of the invention in which incremental truncation resulting in one-nucleotide base deletions are desired.

The fact that the digestion rate of a given nuclease enzyme can be affected by a variety of methods and conditions, such as lowering the incubation temperature, altering the digestion buffer composition, inclusion of a nuclease inhibitor or lowering the ratio of enzyme to nucleic acid, is advantageous to the present invention. Embodiments of the present invention modulate conditions affecting the digestion rate of particular nuclease enzymes so that the degradation is slowed, thus permitting incremental truncation where potentially every nucleotide base can be deleted. The modulation of nuclease enzyme activity is well known to workers of ordinary skill in the art.

The plurality of incrementally truncated nucleic acids, and other incremental truncation modified nucleic acids, can be expressed according to methods well known in the art. For example, expression of the polypeptides encoded by the truncated nucleic acids can be accomplished by an in vitro transcription/translation system. In other embodiments, vectors containing the incrementally truncated nucleic acids can be transformed into an appropriate host for in vivo expression.

The nucleic acids to be expressed can include the necessary regulatory sequences for either in vitro or in vivo expression. For example, promoter sequences, start codons, termination codons, and other similar regulatory sequences can be included in a particular expression vector, based upon the nature of the particular truncated nucleic acid made according to the methods of the present invention.

Transformation of vectors into appropriate hosts is well known in the art. Various methods for the introduction of vectors into host cells are known, including introduction into $CaCl_2$ competent cells, electroporation, direct injection, and the like. Any of these methods is suitable for transforming the plurality of incremental truncation modified nucleic acids into a plurality of particular hosts.

It is possible that more than one construct can be transformed into the same host. This possibility is minimized by, for example, well known techniques such as limiting dilution, use of appropriate vectors such as phagemids, or use of appropriate selection methods.

Techniques for selecting and/or screening transformants are well known in the art. It is to be understood that when selection is referred to herein, the use of screening methods is not ruled out, and vice versa. Generally, both selection and screening methods are used to identify a particular construct of the present invention. However, simply because only the term "selection," or a variant thereof is referred to, a worker of ordinary skill in the art will understand that "selection" often requires "screening," and that "screening" often requires "selection."

For example, a particular vector can carry a kanamycin resistance gene. If such a vector is transformed into a kanamycin-sensitive host, those host cells carrying the vector can be selected by plating the transformants onto a kanamycin-containing growth medium.

Detecting the expression of a particular incremental truncation modified nucleic acid requires screening the selected transformants for a particular activity or functionality. Such screening depends intimately upon the activity or functionality sought. Thus, if the incrementally truncated nucleic acid is to encode some particular enzymatic activity, an appropriate screen for that enzymatic activity is conducted. Examples of selection and screening of a plurality of transformed hosts are presented below.

A variety of truncated nucleic acids can be used to form a plurality of polypeptides that originate from a plurality of differentially modified parent nucleic acids. This plurality of differentially modified parent nucleic acids or polypeptides is sometimes referred to as a library, although the term "plurality" is meant to be broader than, and encompass, the term "library." In certain exemplary embodiments herein, a plurality of incremental truncation modified nucleic acids is sometimes referred to as an incremental truncation library, or ITL.

In general, the members of a library have certain common characteristics. Thus, for example, a library of incremental truncation modified nucleic acids is composed of a plurality of constructs that share common nucleic acid sequences. The difference among the members of the library is the length of each construct.

A plurality of incremental truncation modified nucleic acids does not necessarily possess common characteristics, and therefore is not necessarily a library.

Similarly, a library of hybrid polypeptides of the present invention is composed of a plurality of polypeptides that share common amino acid residue sequences, with the difference among library members being the length of the polypeptide.

In some instances, each member of the library of polypeptides possesses the predetermined characteristic. In this embodiment the libraries are preferably screened or assayed to look for desired activity.

A plurality of polypeptides or hybrid polypeptides of the present invention does not necessarily possess common characteristics such as sequence similarity of functional similarity, and therefore is not necessarily a library.

Once a particular incremental truncation modified nucleic acid construct of the present invention is selected and screened, the construct can be further characterized. For example, the incremental truncation modified nucleic acid can be isolated from a host cell and sequenced using techniques well known in the art. Similarly, the polypeptide expressed by the incremental truncation modified nucleic acid construct can be isolated and sequenced using techniques well known in the art.

In another aspect, the present invention is directed to a method of making a plurality of incrementally truncated hybrid nucleic acids comprising the following steps. A first and second parent nucleic acid is provided. Nucleotides are serially removed from one or both termini of the first and second parent nucleic acids to form truncated first and second parent nucleic acids whose length decreases incrementally over time. The serial nucleotide removal is stopped at a plurality of different times to form a plurality of incrementally truncated first and second parent nucleic acids. Separate incrementally truncated first parent nucleic acids are linked to separate incrementally truncated second parent nucleic acids to form a plurality of incrementally truncated hybrid nucleic acids.

The first and second parent nucleic acids can be chosen independent of homology. The term "independent of homology" is meant to connote that the process of choosing the starting parent nucleic acids is not dependent on homology between nucleic acids. That is, the process can succeed whether or not a substantial degree of homology exists. However, nucleic acids with a high degree of homology, such as homologous genes, can also be employed and this is not excluded by the phrase "independent of homology."

The step of joining can include the step of fusing and/or ligating as described herein. The truncation should be done in a controlled manner that can be time and/or temperature dependent, or otherwise modulated as discussed elsewhere herein.

The plurality of incrementally truncated hybrid nucleic acids includes a plurality of different combined incrementally truncated first and second nucleic acids that can be used later to express polypeptides having different characteristics. Therefore, the plurality of incrementally truncated hybrid nucleic acids can be transformed into a plurality of appropriate hosts, as described elsewhere herein, to form a plurality of transformed incrementally truncated hybrid nucleic acids. This plurality of transformed incrementally truncated hybrid nucleic acids can include a library of transformed incrementally truncated hybrid nucleic acids.

The plurality of incrementally truncated nucleic acids is used to express polypeptides (sometimes referred to herein as hybrid polypeptides) that can have a predetermined characteristic or activity. As is well known in the art, the in vivo expression of a particular nucleic acid sequence depends upon the use of appropriate expression vectors transformed into appropriate hosts. Conditions for appropriate in vitro expression of a given construct are also well known in the art.

Therefore, the polypeptides that are produced by the constructs of the present invention can be selected and/or screened to determine the presence or absence of a predetermined characteristic or activity. It is a preferable aspect of the present embodiment that the selected constructs are screened for activity as well as for the predetermined characteristic.

An important aspect of the present invention is that the hybrid polypeptides that are formed are designed to incorporate inteins or other cleavage producing portions of a protein or polypeptide. These cleavage sites permit the protein or polypeptide to be spliced and recombined to form still further modified hybrid polypeptides that can have a suitable activity.

As used herein, a desired characteristic or desired functionality can include any of the following traits: the absence of a characteristic, function or property; a known and/or unknown function; an increase or a decrease in activity; and novel or unexpected activities.

One theory on the evolution of enzymes posits that catalytic function arises from the interaction of protein fragments that eventually become condensed to a single gene product. The reverse of this process (also referred to as protein fragment complementation) is to convert an existing monomeric enzyme into its functional heterodimer. The use of a plurality of incrementally truncated nucleic acid hybrids, or incremental truncation libraries (ITL), in conjunction with a suitable screen or selection, such as utilizing an auxotrophic host or antibiotic selection, can determine points in the backbone polypeptide chain that can be broken. The two resulting protein fragments still retain the ability to fold and associate into an active heterodimer when a functional selection mechanism is utilized. Importantly, several embodiments of the present invention permit this process of reverse evolution to be performed in vitro in a reasonable amount of time.

Figure 2:
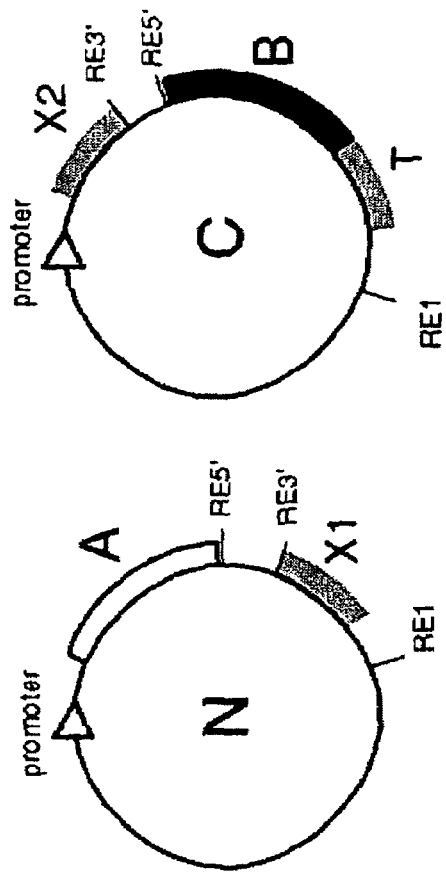
FIG. 2 is a depiction of exemplary vectors used for incremental truncation.

Various features of exemplary vectors utilized for the applications of incremental truncation are shown in FIG. 2. As shown in this figure, plasmids N and C are two compatible vectors with origins of replication belonging to different compatibility groups and bearing genes coding for different antibiotic resistances. For some applications, it is advantageous that the two vectors are phagemids (e.g., that they also contain a phage origin of replication) for packaging into phage particles.

The nucleic acid sequences to be truncated (shown as A and B in FIG. 2) are positioned downstream from a promoter.

The identity of some features of the exemplary vectors is shown in FIG. 1 and depends on the specific application of the method. The X1 and X2 segments (when used) represent the piece of DNA that the ITLs of A or B are fused to in the unimolecular ligation step. The use of 'RE' designates a unique restriction enzyme site. RE5' and RE3' indicate that digestion with the restriction enzyme produces a 5' or 3' overhang respectively. A 5' overhang is susceptible to Exo III digestion whereas a 3' overhang is not susceptible.

An illustration of an application of the principles represented in FIG. 2 involves dividing the gene for a protein (P) into two non-active, overlapping fragments: A (containing the N-terminus of P) and B (containing the C-terminus of P) which are cloned into vectors suitable for incremental truncation.

For this illustration, X1 is a series of stop codons in all three frames, X2 is the start codon ATG, and T is a stop codon in frame with B. After linearizing the vector with restriction enzymes RE3' and RE5' and subsequent incremental truncation, unimolecular ligation results in the 3' end of the ITL of A being fused to a series of stop codons in all three frames and the 5' end of the ITL library of B being fused to a start codon.

Although two-thirds of the ITL library of A have 1-3 foreign amino acids on the end and two-thirds of the ITL library of B are out of frame, one-third of each library is in-frame and not code for any foreign amino acids. Crossing the ITL libraries of A and B by, for example, transforming both libraries into appropriate *E. coli* cells in which the library constructs are expressed, has each cell producing a different combination of an N-terminal fragment and a C-terminal fragment of the original protein, P.

Active members of this crossed ITL library can be identified by screening or selection. This methodology has been applied to *E. coli* glycinamide ribonucleotide transformylase, as reported in Ostermeier et al., *Proc. Natl. Acad. Sci. USA*, 96:3562-3567 (1999), whose disclosure is incorporated by reference herein in its entirety.

Identifying points for functional bisection of an enzyme has applications in enzyme evolution and protein folding, because such bisection points potentially identify ancestral fusion points as well as independent folding units. Such dissection of enzymes into smaller fragments also subverts impediments in the chemical synthesis of enzymes: enzymes too large to be chemically synthesized as a monomer can be synthesized as fragments, thus permitting the introduction of unique side chain functions. Moreover, the identification of functional structural motifs, subdomains, or domains facilitates the construction of hybrid proteins and the creation of proteins with novel activities (e.g., antibiotics with improved effectiveness).

The construction of crossed ITLs of protein structural homologues illustrates one combinatorial approach to domain swapping made feasible by the methods of the present invention.

Bisection of a protein in the manner described above can potentially lead to problems with association of the two fragments, particularly between structural homologues. The two protein fragments can be unable or have little tendency to associate. The addition of tight binding dimerization domains by using a dimerization motif can circumvent this issue.

This type of facilitated association of protein fragments permits the creation of structural-homologue heterodimers. Hybrid proteins can be created such that an ITL of the catalytic machinery of one enzyme (A) is fused to one dimerization domain (X1) and a ITL of a substrate binding domain (B) is fused to a second dimerization domain (X2). Such A-X1 and B-X2 fusion libraries can then be crossed into appropriate *E. coli* cells in which the fusion library constructs are expressed, as described above for example, and the functional association of the two subunits A and B are facilitated by the dimerization of X1 and X2. Although not necessary, X1 and X2 should preferably be different (e.g., they form a heterodimer) so as to avoid homodimerization of A-X1:X1-A and B-X2:X2-B in lieu of heterodimerization (A-X1:X2-B).

Structures such as anti-parallel helixes, parallel helix-turn-helixes and inactive intein domains can also be preferable to avoid the necessity of long linkers. This type of approach permits scanning for novel activities across families of proteins in one experiment, as A and B need not be a discrete genes but can be a library of family members, or a plurality of nucleic acids.

One advantage to this approach is the ability to access very large libraries (about $10^{11}$) if vectors N and C are phagemids and can be packaged into phage particles. Because phage infection is a very efficient method of introducing vectors into E. coli, the library size is limited primarily by the number of E. coli cells in the culture. For example, if each individual A-X1 and B-X2 library has a library size of $2 \times 10^6$, then the crossed library of these two has a maximum library size of $4 \times 10^{12}$. If a liter of $10^{11}$ E. coli cells is infected with phagemid containing each of the ITL-dimer libraries, and 30 percent of the cells become infected with both vectors, then the crossed library size is $3 \times 10^{10}$ Although the ability to use selection on such large libraries can be problematic, such methodology still makes facile the creation of smaller, manageable libraries.

In hybrid polypeptides created by domain swapping, it can be difficult to predict exactly which fusion-points will produce a polypeptide with desired properties. The use of incremental truncation in the creation of hybrid polypeptide libraries solves this problem by a stochastic method.

A novel feature of this method is that it is not dependent upon homology on the nucleic acid level or any knowledge of the structure of either enzyme (or protein). Theoretically, all possible combinations of two genes or two different nucleic acid sequences can be created and, with the use of a suitable screen or selection, active hybrids can be identified. Variations or embodiments of this methodology, which are sometimes referred to herein as Incremental Truncation for the Creation of Hybrid enzYmes, or "ITCHY", are outlined herein.

Seamed ITCHY libraries are created for example, referring to FIG. 2 wherein X1 and X2 are identical restriction sites (RE2) and T is a stop codon in frame with B. The individual ITLs of A and B are constructed as in protein fragment complementation discussed above (e.g., linearization of the plasmid DNA with RE3' and RE5' followed by incremental truncation and recircularization).

Next, the ITL of B is cloned into plasmid N bearing the ITL of A between the RE2 and RE1 sites using identical restriction sites on plasmid C. The resulting ITCHY library is seamed because it contains the restriction enzyme site RE2 (seam) at the junction of the two gene fragments and thus code for foreign amino acids. One third of the library has B in frame with A. If a linker is desired between the two genes, it can be included in either X1 or X2 such that it is between RE2 and the truncated gene.

Seamless ITCHY Libraries are useful for avoiding the seam at the interface between the two truncated nucleic acids. This method, however, depends on the cloning of fragments with one blunt end, so the library size can be less than in a seamed ITCHY.

Figure 3:
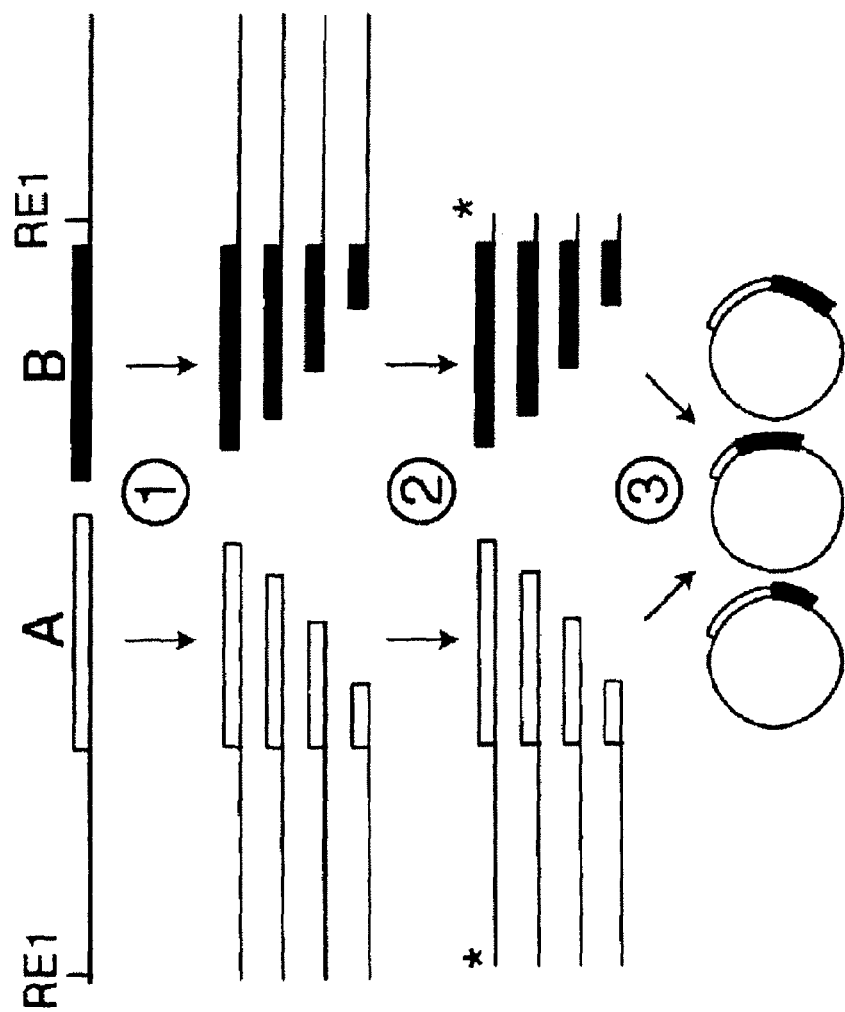
FIG. 3 schematically demonstrates the creation of a seamless ITCHY library.

For example, the linearized versions of vectors N and C from FIG. 2 are prepared by digestion with RE3' and RE5' as shown in step 1 of FIG. 3. Incremental truncation proceeds as in FIG. 1. In step 2 of FIG. 3, the linear ITLs are digested with RE1 and the indicated fragments are isolated. In step 3 of FIG. 3, ligation of the fragments containing the ITL of B into the vector containing the ITL of A proceeds by a sticky end ligation at the site of the asterisk and a blunt end ligation between the truncated genes.

Generally, incremental truncation proceeds as in protein fragment complementation above, except that before the vector is recircularized, plasmids N and C are digested with RE1 (FIG. 3). Vector N (containing the ITL of A) is isolated away from fragment X1 and the ITL of B is isolated from the rest of the vector C. The ITL of B is then ligated into vector N (containing the ITL of A) by a sticky/blunt ligation.

The blunt end ligation is what produces the seamless fusion of the two incrementally truncated genes or nucleic acid sequences. The sticky end ligation (at RE1) provides directionality and improved cloning efficiency (compared to a blunt end ligation). As in a seamed ITCHY, one-third of the library has B in frame with A.

Unlike a seamed ITCHY, a seamless ITCHY is not easily amenable to linker incorporation. For example, seamless ITCHY libraries have been created consisting of up to 7,600,000 fusions (2,530,000 in-frame fusions) between the incremental truncation libraries of two genes. This library size is the theoretical minimum necessary to have all possible fusions between two ITLs whose members contain between 0 and 2,757 deleted bases.

In another aspect of this method, the order in which the two genes or nucleic acid sequences are joined is varied. In a first variant, the plurality of first incrementally truncated nucleic acids (also sometimes referred to herein as the ITL of A) forms the coding region for the N-terminus of the expressed hybrid protein or polypeptide. In a second variant, the plurality of second incrementally truncated nucleic acids (also sometimes referred to herein as the ITL of B) forms the coding region for the N-terminus of the expressed hybrid protein or polypeptide.

In this manner, a seamed or seamless plurality of incrementally truncated hybrid genes can have, as the N-terminal, either the first or second incrementally truncated nucleic acid. The interchangeability of the incrementally truncated nucleic acid portions of the incrementally truncated hybrid nucleic acids increases the number of potential nucleic acid combinations that can be created.

Post-translational protein recombination events can further increase the number of potential hybrid polypeptides that can be created according to methods of the present invention. Protein splicing is a post-translational event involving precise excision of an intein fragment from precursor protein sequences. Although most inteins described to date have been cis-inteins (encoded on one polypeptide), recently engineered and naturally occurring trans-inteins have been described.

The ability of trans-inteins to fuse potentially any two polypeptides is well suited for the creation of hybrid enzyme or protein libraries. A fusion example is shown in FIG. 4.

Figure 4:
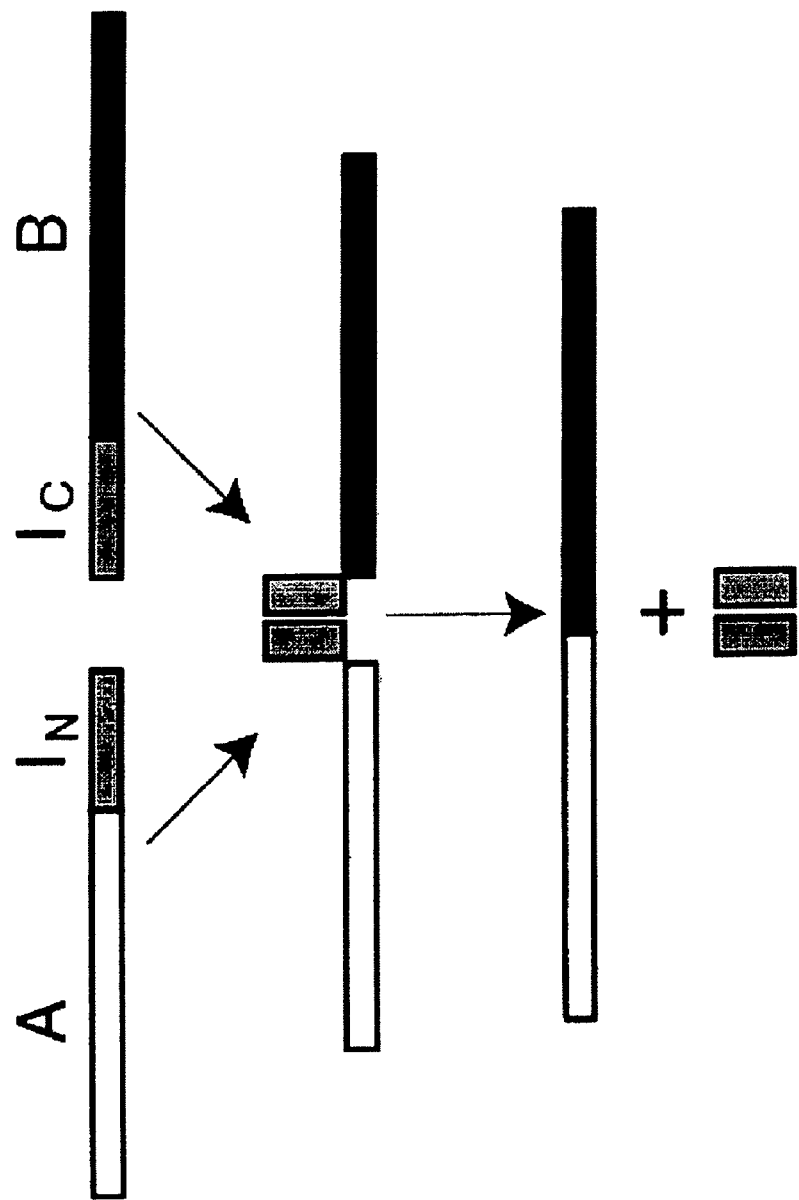
FIG. 4 schematically demonstrates the preparation of a fusion peptide using a trans-intein.

In FIG. 4, fusion proteins of an ITL of A and the N-intein ($I_N$) and of an ITL of B and the C-intein ($I_C$) associate in solution via the interaction of $I_N$ and $I_C$. The intein heterodimer ($I_N$:$I_C$) directs the splicing reaction resulting in the joining of A to B with a native peptide bond and the release of $I_N$:$I_C$.

Generally, in this embodiment, incremental truncation is performed as in the protein fragment complementation described above, resulting in a fusion of an ITL of A to one half of the trans-intein ($I_N$) and an ITL of B to the other half of the trans-intein ($I_C$). If desired, a linker can be incorporated so that either A or B or both are fused to a linker after incremental truncation. Both vectors (containing an ITL fused to an intein or linker-intein) can then be introduced into the same cell and hybrid polypeptide created in vivo as a result of the intein's activity. All the hybrid polypeptide products produced using trans-inteins will necessarily have one residue from the intein at the fusion point.

As in the use of dimerization domains for protein fragment complementation discussed above, one advantage in the use of trans-inteins is that very large hybrid enzyme libraries can be prepared. These libraries are theoretically be much larger than even those made by genetic fusions above (ITCHY libraries).

The successful creation of functional hybrids between two or more genes was historically thought to require a sufficient degree of homology on the DNA level. Current methods of in vitro and in vivo recombination of genes (such as DNA shuffling) depend on the genes having a sufficient degree of homology. However, many interspecies homologues have sequence homology below that which traditional in vitro and in vivo recombination methods can be efficiently performed. That is, on the nucleotide level, there is about 30-40 percent sequence identity.

Proteins with little or no sequence identity, however, can have strong structural homology. The recombination of such genes, for example within a fold superfamily, can result in hybrid proteins with interesting and useful properties. Furthermore, recombination between genes with higher homology at loci of little or no homology can result in hybrid proteins with interesting and useful properties.

Thus, in another aspect of the present invention, a method of recombining nucleic acids that does not require any sequence identity is provided. In this aspect, a method of making a plurality of shuffled incrementally truncated nucleic acids is provided, comprising the following steps. Isolated nucleic acid inserts are provided, preferably of approximately the same length, from a plurality of incremental truncation modified nucleic acids. These isolated nucleic acid inserts are recombined for a time period and under conditions suitable to form a plurality of shuffled incrementally truncated nucleic acids.

In a preferred embodiment, the recombining involves mixing the isolated nucleic acid inserts with a nucleic acid fragmenting enzyme for a time period and under conditions suitable to form a mixture of nucleic acid fragments of the plurality of incremental truncation modified genes. The nucleic acid fragments of the mixture are joined with a nucleic acid ligating enzyme for a time period and under conditions suitable to form a plurality of shuffled incrementally truncated nucleic acids.

This shuffling method uses, as a preferred starting point, either seamed or (preferably) seamless ITCHY libraries as outlined above. More preferably, the starting point is a plurality of first variant incrementally truncated hybrid nucleic acid and a plurality of second variant incrementally truncated hybrid nucleic acids. In other preferred embodiments, the starting point is a plurality of analog-containing incrementally truncated nucleic acid, or a plurality of circular permutation incremental truncation hybrid nucleic acids.

Whereas crossover points between genes in traditional DNA shuffling are defined and confined by the regions of identity, shuffled ITCHY library crossover points are defined by the fusion-points. An ITCHY library theoretically has many, if not substantially all possible crossover points; thus there is no theoretical limitation on the location of crossover points in the resulting hybrid enzyme library. It follows then, that shuffled ITCHY libraries (which are sometimes referred to herein as SCRATCHY libraries) of nucleic acids of high identity can create more diverse libraries than traditional DNA recombination methods.

Figure 5:
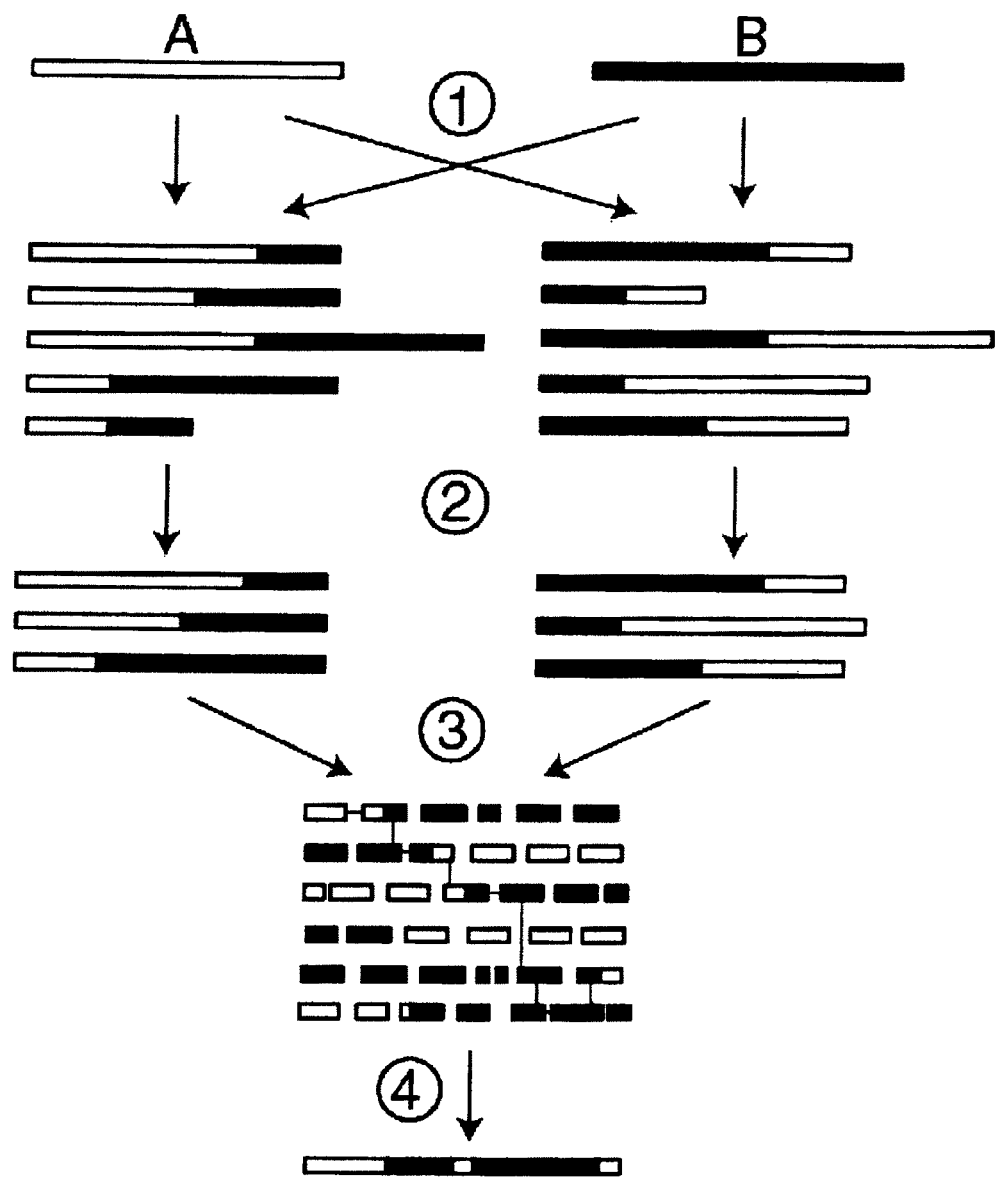
FIG. 5 schematically demonstrates the creation of a SCRATCHY library (created by shuffling two ITCHY libraries)

With reference to FIG. 5, a SCRATCHY library can be created by making two ITCHY libraries: one library formed with gene A on the N-terminus creating A-B fusions, and one library formed with gene B on the N-terminus creating B-A fusions.

Next, DNA fragments of each of the A-B and B-A fusions are isolated. These DNA fragments need not be, but preferably are approximately the same size as the original genes. This can be done by gel electrophoresis or capillary electrophoresis after restriction enzyme digestion (and judicious location of restriction sites) or after PCR with primers near or just outside the ends of fused genes. This step attempts to ensure that the pool of DNA to be shuffled contains fusions at points on the primary and three-dimensional structures that are near each other (i.e., limit crossover points to 'intelligent' locations).

Thus, the SCRATCHY methodology is preferably done with genes A and B being roughly the same size. This DNA with "intelligent" crossover points can then be amplified by PCR to obtain enough sample to perform DNA recombination, or shuffling. The two libraries (that include A-B and B-A PCR products of approximately the same size as the original genes) are then mixed, can then be subsequently digested with DNase I, and can be followed by a method for in vitro or in vivo recombination.

Such methods for in vitro or in vivo recombination include the following methods. DNA shuffling is exemplified by Stemmer, Proc. Natl. Acad. Sci. USA 91:10747-10751 (1994), whose disclosure is incorporated in its entirety herein by reference.

Molecular breeding, also known as family DNA shuffling or sexual PCR, is exemplified by Crameri et al., Nature 391: 288-291 (1998), whose disclosure is incorporated in its entirety herein by reference.

Staggered extension process (StEP) is exemplified by Zhao et al., Nature Biotech. 16:258-261 (1998), whose disclosure is incorporated in its entirety herein by reference.

Random-priming in vitro recombination is exemplified by Shao et al., Nucl. Acids Res. 26(2):681-683 (1998), whose disclosure is incorporated in its entirety herein by reference.

DNA reassembly by interrupting synthesis is exemplified by U.S. Pat. No. 5,965,408, issued Oct. 12, 1999 to Short, whose disclosure is incorporated in its entirety herein by reference.

Random chimeragenesis on a transient template (RACHITT™) (Enchira Biotechnology Corp.; The Woodlands, Tex.) is exemplified by W. M. Coco et al., "A Novel Method of Gene Family Shuffling Relieves Simultaneous Bottlenecks in a Highly Engineered Pathway," presented at the Society of Industrial Microbiology 2000 Annual Meeting, July 23-27, San Diego, Calif., whose disclosure is incorporated in its entirety herein by reference.

PCR-mediated recombination is exemplified by Judo et al., Nucl. Acids Res. 26(7):1819-1825 (1998).

Recombination can also occur by in vivo recombination methods, which are well known in the art.

FIG. 5 shows an example of non-homologous shuffling or recombination of ITCHY libraries, wherein step 1 illustrates that individual A-B and B-A ITCHY libraries are constructed, for example, as shown in FIG. 3.

Step 2 illustrates that either through use of outside restriction enzymes or outside PCR primers, those members of the ITCHY libraries that are approximately the same size as the original genes are isolated by gel or capillary electrophoresis. In step 3, these selected ITCHY library members are mixed and fragmented by digestion with DNase I as in traditional methods of DNA recombination. In step 4, reassembly of the random fragments can proceed by template switching that can result in full-length genes with multiple crossovers.

The number of hybrids appearing "in frame" decreases exponentially with total number of crossovers. For example, the original ITCHY libraries only have one-third of the hybrids in-frame. A resulting member of the SCRATCHY library with two crossovers only has a 1 in 9 chance of being completely in-frame, with three crossovers having only 1 in 27 completely in-frame.

This circumstance can be addressed by pre-selecting the original ITCHY libraries for hybrids in frame. For example, if gene B is fused in frame to a reporter gene with a selectable phenotype, then all in frame ITCHY library members with in-frame crossover points can be selected. The reporter gene need not be a part of the final SCRATCHY library because it can be easily removed in the PCR steps prior to DNase I digestion. In-frame fusions have been selected for in two different ITCHY libraries by this method using the neomycin resistance gene as the reporter gene.

Another embodiment of the invention includes the pairing of (a) an analog of a ribonucleotide or deoxyribonucleotide (sometimes referred to herein as a nucleotide analog) that can be randomly incorporated into double-stranded nucleic acids by a nucleic acid polymerase and (b) an enzyme with 3' to 5' exonuclease activity that is not capable of excising the incorporated nucleotide analog.

In this aspect, the present invention provides a method of making a plurality of analog-containing incrementally truncated hybrid nucleic acids comprising the following steps. A plurality of nucleotide analog-containing parent nucleic acids is provided. Nucleotides are removed from the plurality of nucleotide analog-containing parent nucleic acids with a nuclease enzyme that does not depolymerize nucleotide analogs incorporated into a nucleic acid. The nuclease enzyme is used under conditions and for a time period sufficient to form a plurality of analog-containing truncated nucleic acids.

The plurality of nucleotide analog-containing parent nucleic acids preferably comprises a plurality of nucleotide analog-containing incremental truncation modified nucleic acids. More preferably, the plurality of nucleotide analog-containing parent nucleic acids comprises a plurality of nucleotide analog-containing shuffled incrementally truncated nucleic acids.

As noted, the nucleotide analog is capable of being incorporated into a nascent nucleic acid strand using a nucleic acid polymerase such as DNA polymerase or RNA polymerase. For example, a parent nucleic acid is provided, and nucleotides are then removed from one or both termini of the parent nucleic acid to form truncated parent nucleic acids. Complementary nucleic acid strands are resynthesized on the truncated parent nucleic acids with a nucleic acid polymerizing enzyme in the presence of nucleoside triphosphates (NTPs or dNTPs) and nucleotide analogs under conditions and for a time period sufficient to form a plurality of nucleotide analog-containing parent nucleic acids.

In another example of incorporation of nucleotide analogs into a nucleic acid, a parent nucleic acid can be amplified using well-known PCR techniques. The PCR amplification is done in the presence of nucleoside triphosphates (NTPs or dNTPs) and nucleotide analogs under conditions and for a time period sufficient to form a plurality of nucleotide analog-containing parent nucleic acids.

The parent nucleic acid into which nucleotide analogs are incorporated can comprise an incremental truncation modified nucleic acid, thereby forming a plurality of nucleotide analog-containing incremental truncation modified nucleic acid.

The nucleotide analog is resistant to depolymerization by an enzyme that depolymerizes nucleic acids, such as an exonuclease. The nucleotide analog is resistant to depolymerization because it is not recognized by an exonuclease, or it forms internucleotide bonds that are substantially resistant to cleavage by an exonuclease. For example, nucleotide analogues can have pseudophosphate bonds that are resistant to exonuclease or endonuclease cleavage, but that still allow their incorporation into a nascent nucleic acid chain.

Such nucleotide analogs are well known in the art. Exemplary pseudophosphate bonds include, but are not limited to, methylphosphonate, phosphomorpholidate, phosphorothioate, phosphorodithioate and phosphoroselenoate bonds.

Additionally, exonuclease- and/or endonuclease-resistant polynucleotides can be obtained by blocking the 3'- and/or 5'-terminal nucleotides with substituent groups such as acridine, caps such as 5-methylguanosine or poly(A) tails, as are well known in the art. See, e.g., Cohen (ed.), Oligodeoxynucleotides, CRC Press, Boca Raton, Fla. (1989); Gait (ed.), Oligonucleotide Synthesis: A Practical Approach, IRL Press, Oxford, England (1984).

Preferred pseudophosphate bonds are phosphorothioate bonds.

A preferred nucleotide analog is a phosphorothioate-containing nucleotide.

This embodiment of the invention provides for: (i) the creation of an incremental truncation library without requiring the labor intensive, time consuming process of taking timed aliquots during exonuclease digestion; (ii) the creation of ITCHY libraries on a single vector avoiding purification of desired fragments; (iii) the controlled incorporation of point mutations into incremental truncation or ITCHY libraries during a polymerase-catalyzed fill-in reaction; (iv) minimizing the biases in truncation length inherent in the other embodiments previously discussed; and (v) minimizing the number of steps required and the time required to construct an incremental truncation or ITCHY library.

Figure 6A:
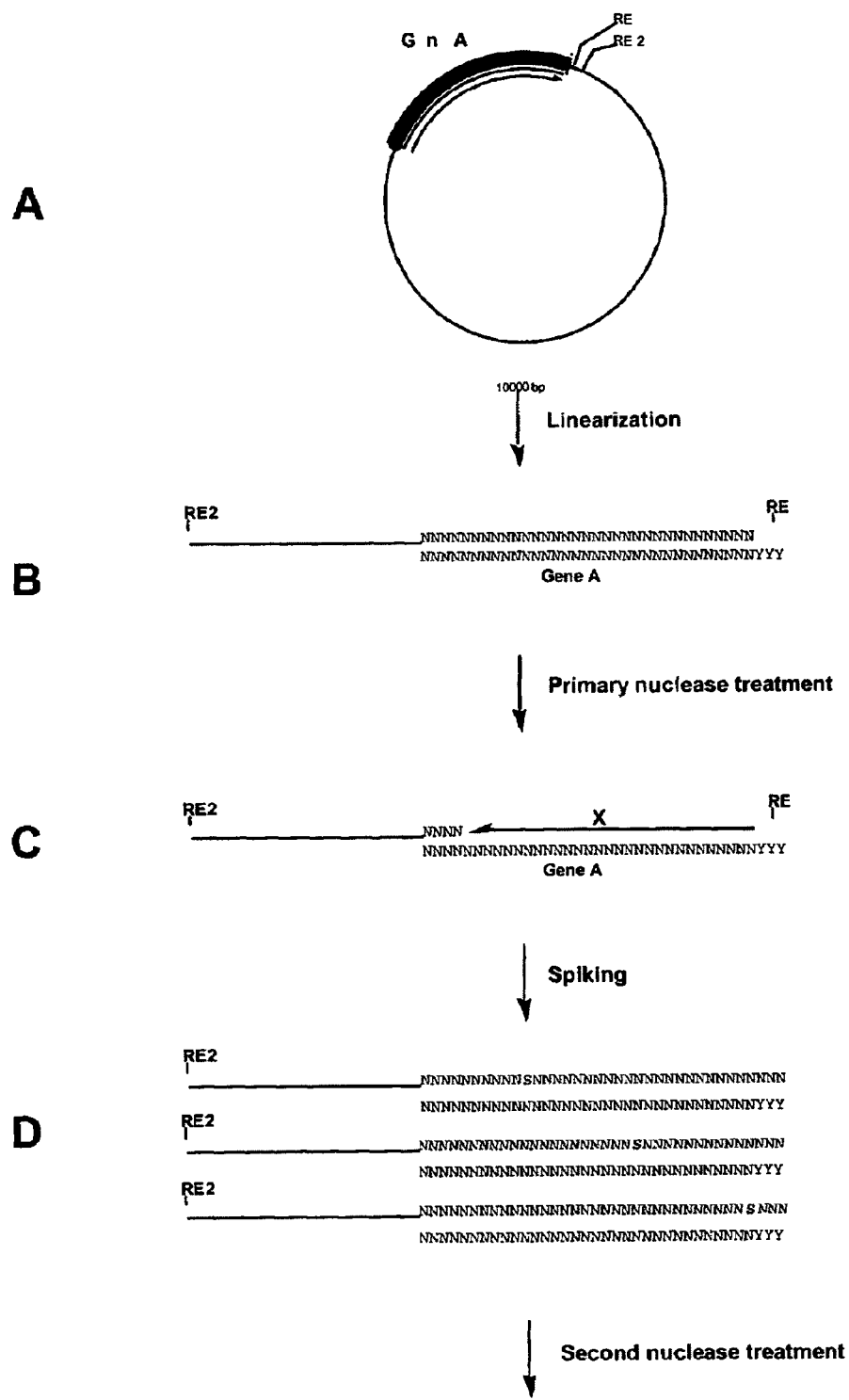
FIG. 6 is a depiction of a parental incremental truncation plasmid and construction of an incremental truncation library using nucleotide analogs.
Figure 6B:
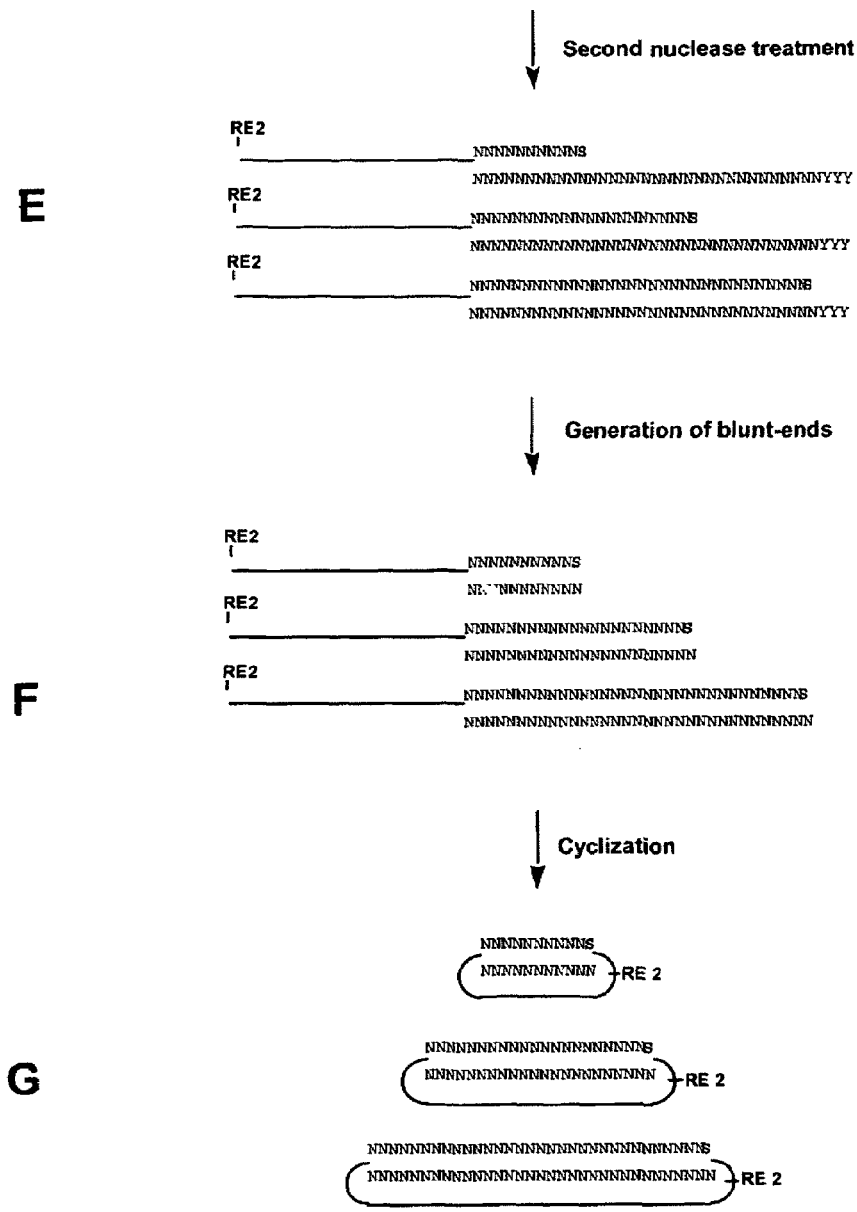

With reference to FIG. 6, the parental ITCHY plasmid is linearized by digestion with a pair of restriction endonucleases (RE's) that cut at unique sites in the plasmid, and thus generate a recessive 3'-terminus (or flush ended terminus) (Y) at the end to be truncated, and an hydrolysis-resistant terminus (RE 2) including, but not limited to a recessive 5'-terminus, at the other end.

Primary nuclease treatment can be carried out by an enzyme with 3' to 5' exonuclease activity, including, but not limited to Exo III. The same enzyme can then be used to perform the primary digestion of the linearized plasmid. The reaction conditions (such as temperature and salt concentration) are used to adjust the reaction rate. For example, at 22° C. and at a salt concentration of 100 millimolar NaCl a digestion rate of approximately 10 nucleobases/minute results for exonuclease III.

The linearized plasmid is incubated with the 3' to 5' exonuclease to generate a single-stranded overhang. Shown as X in FIG. 6C, the length of the truncated region and the digestion or cutback rate (as discussed above) determine the incubation time required. In contrast to other methods to generate incremental truncation libraries described herein, only a single timepoint need be taken in order to obtain a full range of truncated products.

The single-stranded portion of the plasmid, produced by nuclease treatment, is used as the template for the resynthesis of the complementary DNA strand. In one embodiment, the reaction requires an enzyme with 5'-3' polymerization activity, appropriate metal ions, and nucleoside triphosphates. The nucleoside triphosphates in the reaction are preferably a mixture of the natural deoxyribonucleotides (dATP, dCTP, dGTP, dTTP) or ribonucleotides (ATP, CTP, GTP, UTP) and nucleotide analogs (shown as S in FIG. 6D), which is referred to as spiking the reaction. The nucleotide analogs are incorporated at random during the synthesis of the complementary strand as depicted by three representative sequences shown in FIG. 6D.

The polymerization can be catalyzed by a DNA polymerase, including for example the Klenow fragment of *Escherichia coli* DNA polymerase I, Taq DNA polymerase, T4 DNA polymerase, Vent™ DNA polymerase, and Pfu DNA polymerase. Preferably, a polymerase that lacks 3' to 5' exonuclease activity is used. Utilizing a thermostable enzyme, such as Taq DNA polymerase, has the advantage of reducing the formation of secondary structure within the single-stranded sequence, which could interfere with primer extension.

Preferably, appropriate metal ions, including but not limited to magnesium and manganese, are present in the complementary strand extension reaction. A single metal ion or a mixture of two or more metal ions can be added to the reaction mixture to vary the fidelity of the extension according to methods known in the art.

Thereafter, all four natural deoxyribonucleoside triphosphates (dATP, dGTP, dCTP, and dTTP) or ribonucleoside triphosphates (ATP, GTP, CTP, UTP), as well as the nucleotide analogs (including but not limited to α-phosphorothioate deoxynucleoside triphosphates) are mixed in a concentration ratio, determined by the length of the primary nuclease treatment (shown as X in FIG. 6C) so as to incorporate, on average, a single nucleotide analog over the entire length of the resynthesized complementary strand. The ratio for the nucleotide triphosphates to analogs can be calculated by the following equation:

$$\frac{1}{X}\delta[C] = [S] \quad (1)$$

$X$ = length of primary nuclease digestion $\delta$ = correction factor $[C]$ = concentration of *dNTPs*

$[S]$ = concentration of *α-S-dNTPs*

The correction factor δ is readily determined experimentally for the individual nucleotide analog that is used in the spiking reaction. The correction factor reflects the efficiency by which the nucleotide analog is utilized by the polymerase in comparison to the natural nucleoside triphosphates.

To illustrate the above equation, a primary digestion with Exo III over approximately 300 nucleotides (X=300) would set the concentrations of the reactant as following: at a concentration of 200 micromolar for each dNTP ([C]) and δ=1, the concentration of each α-S-dNTPs ([S]) would be 0.67 micromolar.

The reaction mixture is then incubated at a temperature appropriate for double-strand synthesis by the enzyme. The temperature therefore can, but need not necessarily, be set at the manufacturer-recommended activity optimum, giving access to additional random mutations under suboptimal reaction conditions.

As noted above, PCR amplification can be used to incorporate nucleotide analogs into nucleic acids to form nucleotide analog-containing parent nucleic acids. The same considerations as discussed above in the context of primer extension apply here as well. However, PCR amplification provides certain advantages. For example, only nanogram quantities of starting nucleic acids are required for PCR amplification. In addition, PCR manipulations require less "hands-on" time.

In addition, consideration must be given to the length of the starting nucleic acids and to the potential for introduction of point mutations throughout the amplified DNA. These point mutations can be desirable, because they increase the diversity of the starting parental nucleic acids and concomitantly in the final truncated products. These point mutations can also disrupt or modulate other functional elements on the starting nucleic acids. Therefore, in some cases, subcloning of the truncation library into a separate expression system is necessary.

Where further mutational diversity is desired in PCR amplification, the fidelity of the polymerase during primer extension (as well as amplification) can be varied by partial substitution of magnesium with manganese. Reaction buffer composition and reaction temperature can also be modulated to increase mutation frequency to desirable levels. See, Cadwell and Joyce, *PCR Methods and Applications,* 3:S136-S140 (1994).

After completion of double-strand synthesis as shown in FIG. 6D (or PCR amplification, as discussed above), the analog-spiked linearized plasmid is incubated with an enzyme with 3' to 5' exonuclease activity (that carries out a second nuclease treatment) that is unable to hydrolyze the nucleic acid beyond the analog, such as Exo III, for example. Based on the random incorporation of the analog during the previous resynthesis of the complementary nucleic acid strand, the hydrolysis is terminated at the position of the nucleotide analog over the entire length of X, as shown by the three representative sequences shown in FIG. 6E, for example.

The reaction conditions for the second nuclease treatment are somewhat less critical than those of the first nuclease treatment. The RE2-site is protected from hydrolysis and the digestion by the 3' to 5' exonuclease is automatically terminated upon encountering the nucleotide analog in the nucleic acid strand.

With reference to FIG. 6F, after the second nuclease treatment, the single-stranded portions of the plasmid are degraded upon addition of a nuclease that specifically hydrolyses single-stranded nucleic acid, for example S1 nuclease or mung bean nuclease, thereby providing blunt ends.

To improve the cyclization efficiency, the plasmid can be briefly incubated with a nucleic acid polymerase, preferentially the Klenow fragment of *E. coli* DNA polymerase I, in the presence of appropriate metal ions and the natural deoxyribonucleoside or ribonucleoside triphosphates, as is well known.

The blunt-ended truncated library can then be recyclized as shown in FIG. 6G, using chemical or enzymatic methods, including for example nucleic acid ligases such as $T_4$ DNA ligase, at the conditions recommended by the manufacturers.

Figure 7A:
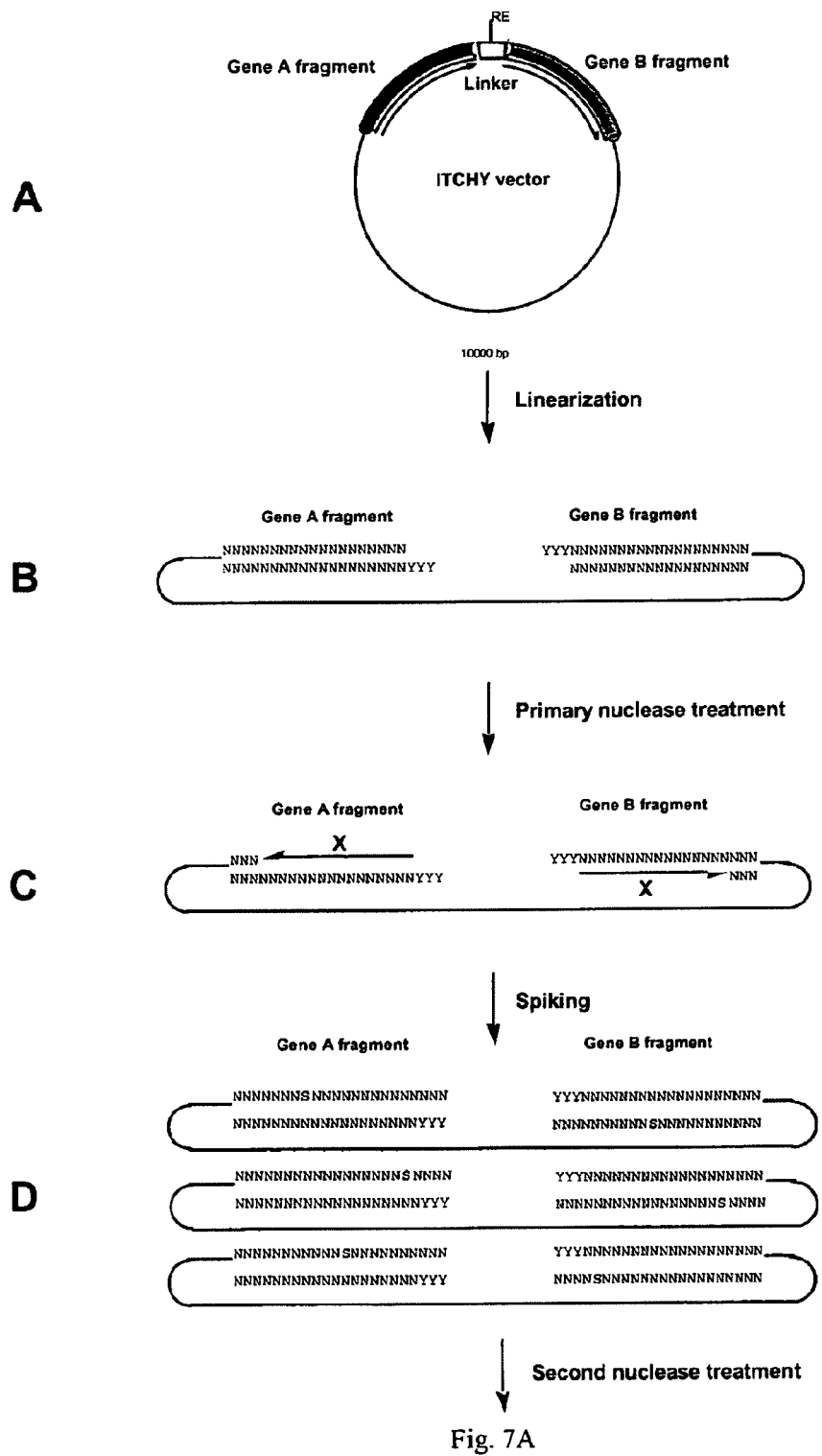

The following discussion further demonstrates the construction of fusion protein libraries between two nucleic acid sequences (for example, individual genes or gene fragments), located on a single plasmid, as shown in FIG. 7A, by simultaneous incremental truncation.

Figure 7B:
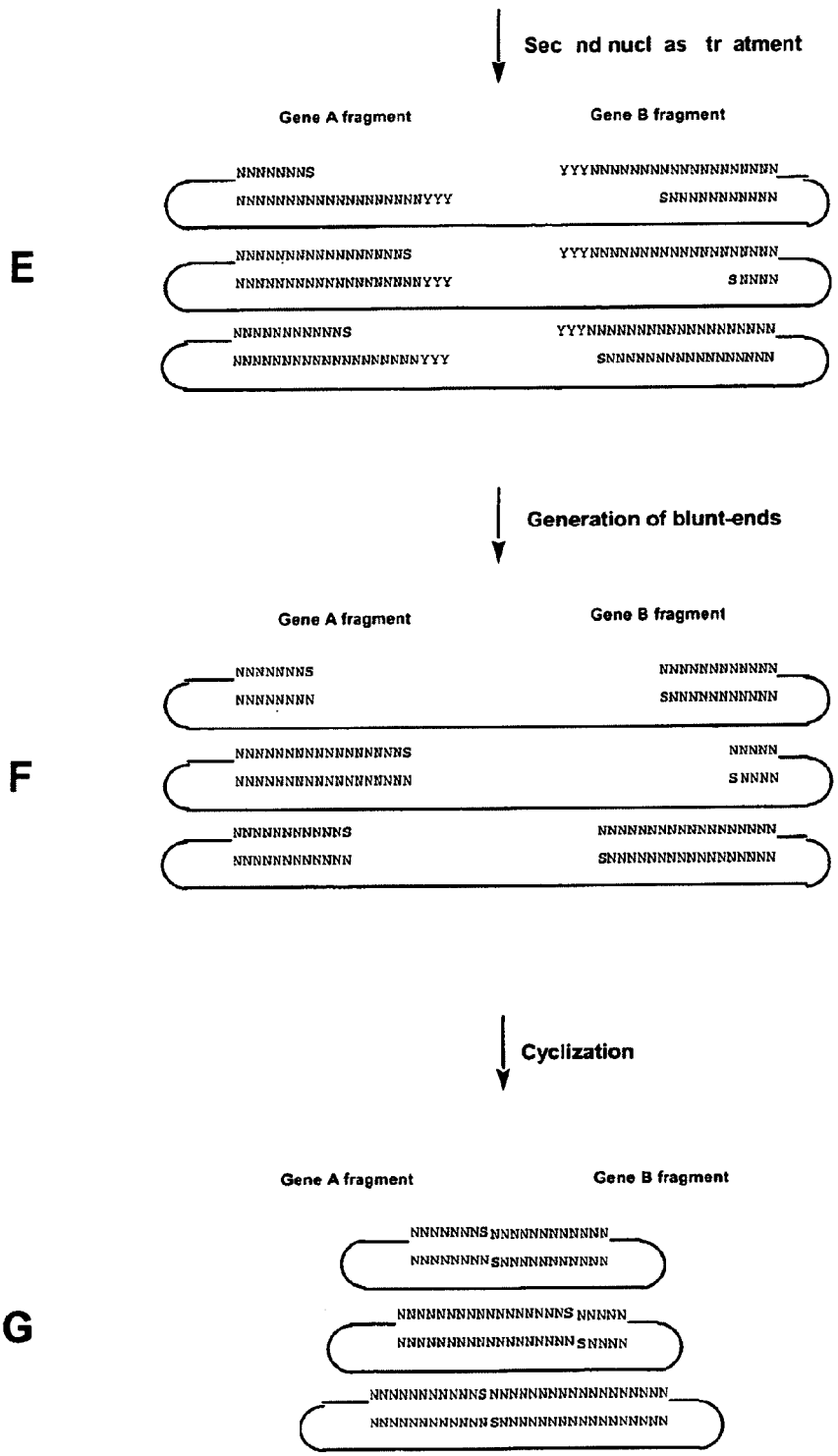

Under these specific conditions, the linearization can be achieved with a single restriction endonuclease that produces a recessive 3'-termini or a flush-ended termini as symbolized by "Y" in FIG. 7B.

Upon incubation with a 3' to 5' exonuclease, (for example Exo III) gene or gene fragment A and B are hydrolyzed simultaneously over the distance X, generating a stretch of single-stranded nucleic acid. The length of X can be controlled by the reaction conditions, including but not limited to such elements as the enzyme, the composition of the reaction buffer, the reaction temperature, and the incubation period.

Resynthesis of the complementary nucleic acid strand by a nucleic acid polymerase, (for example the Klenow fragment of *E. coli* DNA polymerase I, or Taq DNA polymerase) in the presence of appropriate metal ions and a mixture of natural deoxyribonucleoside or ribonucleoside triphosphates and nucleotide analogs (symbolized S) in the appropriate ratio (see the above equation (1) for guidelines to determine the calculation of the required nucleotide analog concentration) leads to the random incorporation of nucleotide analogs in both directions over the entire stretch (X) of the resynthesized complementary nucleic acid strand, as shown in FIG. 7D. As mentioned elsewhere herein, a series of variables can be used to further randomize the nucleic acid at this stage, including such elements as the type of nucleic acid polymerase, the reaction buffer composition, the metal ion(s) present in the reaction mixture, and the reaction conditions in general.

After completion of double-strand synthesis (FIG. 7D), the nucleotide analog-spiked linearized plasmid is incubated with an enzyme with 3' to 5' exonuclease activity that is unable to depolymerize the nucleic acid beyond the nucleotide analog (e.g., Exo III). Based on the random incorporation of the nucleotide analog during the previous resynthesis of the complementary nucleic acid strand, the simultaneous hydrolysis in both directions will be terminated at the random positions of the nucleotide analog, as depicted by three representative sequences shown in FIG. 7D.

The reaction conditions for the second nuclease treatment represented in FIG. 7E, are less critical. The digestion by the 3' to 5' exonuclease will automatically be terminated upon encountering the nucleotide analog in the nucleic acid strand.

Following the second nuclease treatment, all single-stranded portions of the plasmid are degraded upon addition of a nuclease that specifically hydrolyses single-stranded nucleic acid, such as S1 nuclease or mung bean nuclease (FIG. 7F).

To improve the cyclization efficiency, the plasmid can be briefly incubated with a nucleic acid polymerase, preferentially the Klenow-fragment of *E. coli* DNA polymerase I, in the presence of appropriate metal ions and the natural deoxyribonucleoside or ribonucleoside triphosphates.

The blunt-ended truncated library is recyclized using chemical or enzymatic methods, including but not limited to nucleic acid ligases, preferentially T4 DNA ligase, at the conditions recommended by the manufacturers (FIG. 7G).

In a further embodiment, as discussed above, the spiking with nucleotide analogs can be carried out by PCR amplification. A parental nucleic acid (such as DNA) target is amplified with 5' and 3' outside primers in the presence of NTPs or dNTPs and one or more nucleotide analogs, using a nucleic acid polymerase (including but not limited to Taq DNA polymerase) preferentially with no exonuclease activity. The ratio between natural base and analog is such that on average only a single analog is incorporated per region to be truncated. Reaction conditions (for example reaction buffer composition, reaction temperature, metal ions (for example magnesium and manganese)) can be varied to affect the fidelity of the primer extension and lead to customizable levels of random mutagenesis during amplification according to methods known in the art.

A unique restriction site that affords protection to truncation is located at the end of the PCR product that is not to be truncated. Following restriction digestion with this restriction enzyme, the amplification product is incubated with an enzyme with 3' to 5' exonuclease activity that is unable to hydrolyze the nucleic acid beyond the analog (for example exonuclease III). Alternatively, it may be desirable for the truncation to be performed simultaneously from both ends if for example the restriction enzyme digestion is omitted.

The single-stranded portion of the amplification product is degraded with nuclease that specifically hydrolyzes single-stranded nucleic acid, for example S1 nuclease or mung bean nuclease generating blunt ends. To further increase the ratio of blunt ends, the amplification product is briefly incubated with a nucleic acid polymerase, preferentially the Klenow fragment of *E. coli* DNA polymerase I, in the presence of appropriate metal ions and the natural nucleotides.

The fragment nucleic acid library can then be cloned into a suitable vector, which may or may not contain a previously prepared nucleic acid library, according to methods known to the art.

In another aspect, the present invention provides a method of creating a circular permutation incremental truncation hybrid nucleic acid comprising the following steps. Isolated first and second nucleic acids are provided. A plurality of circularly permuted nucleic acid fragments, each of which contains a randomly located restriction enzyme site, is inserted between the first and second nucleic acids to form a plurality of circular permutation hybrids. The plurality of circular permutation hybrids is reacted with a restriction enzyme that recognizes and specifically hydrolyzes the randomly located restriction enzyme site for a time period and under conditions sufficient to form a plurality of circular permutation incremental truncation substrates. Nucleotides are then removed from both ends of the restriction enzyme site to form a plurality of circular permutation incrementally truncated hybrids. The nucleotide removal is then stopped to form a plurality of circular permutation incrementally truncated hybrid nucleic acids having a gap. The gap is then closed to form a plurality of circular permutation incremental truncation hybrid nucleic acids.

Figure 8:
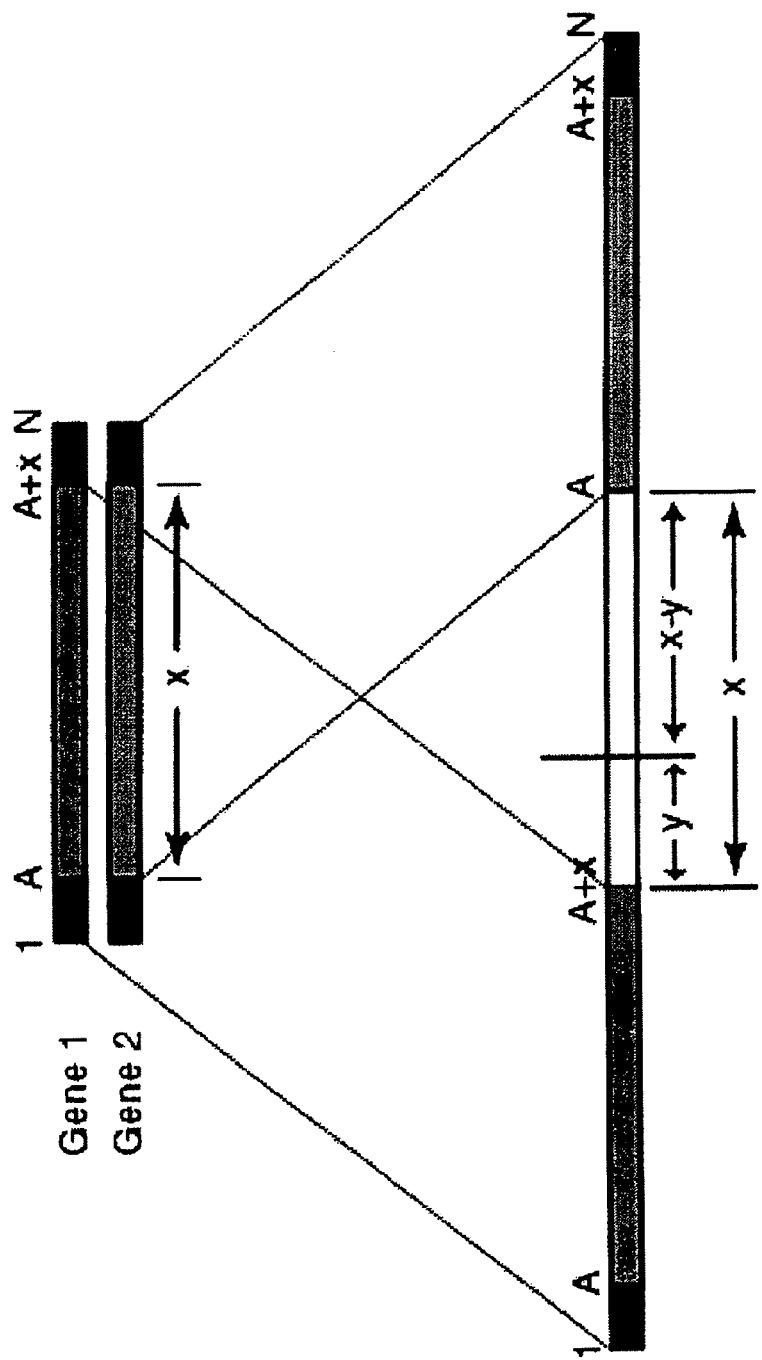
FIG. 8 is an illustration of the CP-ITCHY principle.

This method is sometimes referred to herein as circular permutated ITCHY (CP-ITCHY). CP-ITCHY is a modification of previously described methods that offers a number of advantages. The general principle of this method is represented in FIG. 8. The two nucleic acids (for example, two genes denominated gene 1 and gene 2) are preferably of approximately the same length (N).

In this embodiment, it is desired to make a plurality or library of possible fusions between N-terminal fragments of gene 1 and C-terminal fragments of gene 2, preferably at or near where the two genes align. The region chosen to make the fusions is therefore preferably between position A and position A+x.

A vector is constructed containing the indicated fragments of the two nucleic acid sequences (e.g., two genes), from position 1 to position A+x of gene 1 and position A to position N of gene 2. A piece of DNA (CP-insert, also referred to herein as a circularly permuted insert or circularly permuted nucleic acid fragment) is inserted between these two nucleic acid fragments. This inserted nucleic acid fragment is of length x with a unique restriction site y bases from the fragment of gene 1.

If the vector is opened up at this unique restriction site and the nucleic acid is truncated with Exo III in both directions for the amount of time necessary to truncate x bases, truncation will arrive at position $(A+x+y)-x=A+y$ in gene 1 and position $(A-(x-y))+x=A+y$ in gene 2. If the DNA of length x is a plurality of nucleic acid fragments containing this restriction site located randomly between y=0 and y=x, then truncation of this vector for x bases in each direction will result in a plurality of most, if not substantially all, possible fusions between gene 1 and 2 between A and A+x at or near where the two genes align.

As noted, between the two (preferably overlapping) fragments of the two nucleic acid sequences to be fused is located a piece of DNA (CP-insert) of length equal to the overlap in the two fragments. The CP-insert has a unique restriction site randomly located within. This restriction site is the start of truncation in both directions.

A sample vector for creating CP-ITCHY libraries is shown in FIG. 9a. The vector has an antibiotic resistance gene (ampicillin; Ap) as well as the two nucleic acid sequences (in this example, the gene fragments PurN[1-202] and GART[20-203]) cloned downstream of a suitable promoter (lac P/O). Between the two gene fragments is located a unique restriction enzyme site that produces blunt ends (EcoRV). This is the site of the insertion of a circularly permuted nucleic acid fragment.

The methodology for creating the CP-insert and the CP-ITCHY library is described in FIG. 9b. The CP-ITCHY library is prepared by amplifying by PCR, or similar technique, a piece of DNA equal in length to the overlap between the two gene fragments and creating a unique restriction site at both ends (in this case XbaI) and cloning this DNA fragment into a suitable vector such as pUC19. The DNA is multiplied and excised from pUC19 using XbaI and treated with ligase under dilute conditions such that a significant amount of closed circular DNA is formed.

The closed circular DNA is linearized at random sites by digestion with very dilute amounts of DNase I. The gaps, nicks and/or termini of the resulting randomly linearized DNA are repaired using a DNA polymerase and DNA ligase and cloned into the EcoRV site of pDIM-N5 by blunt end ligation. The result is a plurality of circular permutation hybrids comprising randomly located XbaI sites between the two gene fragments. This plurality of circular permutation hybrids is the source DNA for incremental truncation.

The plurality of circular permutation hybrids is digested with XbaI to linearize the vectors, and digested with Exo III for the length of time described in FIG. 8. After this digestion, two ends are left, separated by a gap. The single stranded overhangs are removed by mung bean nuclease, the ends are blunted with the Klenow fragment and ligation of the treated ends under diluted conditions to close the gap between the ends results in the CP-ITCHY library (or a plurality of circular permutation incremental truncation hybrid nucleic acids).

The principle advantages of CP-ITCHY are (a) only one vector is required, (b) truncation occurs in both directions simultaneously, (c) does not require extensive time point sampling, (d) biases the library considerably towards fusions at or near where the sequences align (i.e., where it is most likely to produce active fusions), and (e) the method does not require certain time-consuming manipulations such as extracting DNA from agarose electrophoretic gels.

Particular incremental truncation modified nucleic acids, or incrementally truncated polypeptides or proteins, or hybrid polypeptides or proteins, made by the methods of the present invention, are also contemplated herein. Thus, once a particular incremental truncation modified nucleic acid construct is made according to a method of the present invention, it is contemplated that such construct can be transformed into an appropriate host for further manipulation.

The transformed constructs themselves therefore constitute one aspect of the present invention. The transformed constructs can be selected or screened, as described elsewhere herein, to give rise to a particular transformed incremental truncation modified nucleic acid having the desired characteristics. This particular transformed incremental truncation modified nucleic acid is contemplated in one aspect of the present invention.

The constructs themselves, once selected or screened, can be expressed as truncated polypeptides or hybrid polypeptides. Expression of truncated polypeptides or hybrid polypeptides in vivo or in vitro is discussed elsewhere herein. A particular expressed truncated polypeptide or hybrid polypeptide is also contemplated as an aspect of the present invention.

Pluralities and libraries of the various hybrid nucleic acids and hybrid polypeptides are contemplated as further aspects of the present invention. Thus, the present invention contemplates a plurality of expressed truncated parent nucleic acid products. In another aspect, the present invention contemplates a plurality of incrementally truncated hybrid nucleic acids. In a still further aspect, the present invention contemplates a plurality of first variant incrementally truncated hybrid nucleic acids. In yet another aspect, the present invention contemplates a plurality of second variant incrementally truncated hybrid nucleic acids. In a still further aspect, the present invention contemplates a plurality of shuffled incrementally truncated hybrid nucleic acids. In a yet further aspect, the present invention contemplates a plurality of analog-containing incrementally truncated nucleic acids. In a still further aspect, the present invention contemplates a plurality of circularly permuted incrementally truncated hybrid nucleic acids.

Various kits that are generally useful for producing or constructing the various incremental truncation modified nucleic acids and/or hybrid polypeptides described herein are also contemplated. Additional kits may be useful for making incremental truncation libraries and/or for producing a plurality of truncated recombinant plasmids. Useful components of such kits can include the following components:

(a) a purified exonuclease reagent (such as Exo III) that removes nucleotide bases in a target nucleic acid fragment;

(b) a recombinant vector molecule such as a plasmid or a bacteriophage vector (particularly useful ones include pDIMN2, pDIMC8, pDIMN5, pDIMN6, pDIMC9 some of which are described in Ostermeier M, Shim J H, and Benkovic S J, Nat. Biotechnol., 17(12):1205-9 (1999), which is incorporated herein by reference in its entirety) [additional useful features of the recombinant vector molecules as described in (b) above, can include restriction sites, potential sequencing primer binding sites, a multiple cloning site, an antibiotic resistance marker, and/or a regulatable promoter];

(c) a single-strand specific nuclease enzyme such as mung bean nuclease or S1 nuclease;

(d) buffer solutions useful in the kits can include exonuclease digestion buffers, a single-strand specific nuclease digestion buffer, a single-strand specific nuclease termination (stop) buffer, an exonuclease termination (stop) buffer, a nucleic acid polymerase buffer and/or a nucleic acid ligase buffer;

(e) nucleic acid polymerases useful in the kits can include a DNA polymerase such as the Klenow fragment or Taq DNA polymerase or an RNA polymerase;

(f) further elements of the kits may include a mixture of NTPs or dNTPs at a specific concentration; nucleotide analogs; a nucleic acid ligase such as T4 DNA ligase or other suitable ligase; and a suitable host for selecting a protein of desired functionality.

It is to be understood that such a kit is useful for any of the methods of the present invention. The choice of particular components is dependent upon the particular method the kit is designed to carry out.

In particularly preferred embodiments, the kit can be packaged in a single enclosure including instructions for performing the methods of the present invention. In some embodiments, the reagents are provided in containers and are of a strength suitable for direct use or use after dilution.

In one preferred embodiment, a kit includes a purified exonuclease reagent, a vector, and appropriate buffers. A preferred buffer is an exonuclease digestion buffer. A further preferred buffer is an exonuclease termination buffer.

In a further preferred embodiment, a kit includes a purified exonuclease reagent, a vector, a single-strand specific nuclease, and appropriate buffers. Preferred buffers include an exonuclease digestion buffer and a single-strand specific nuclease digestion buffer. Further preferred buffers include an exonuclease termination buffer and a single-strand specific nuclease termination buffer.

In a still further preferred embodiment, a kit includes a purified exonuclease reagent, a polymerase, a nucleotide analog, and appropriate buffers. A preferred buffer is an exonuclease digestion buffer. A further preferred buffer is an exonuclease termination buffer. A still further preferred buffer is a polymerase buffer. A preferred nucleotide analog is a phosphorothioate-containing nucleotide analog. The kit further optionally contains a mixture of NTPs or dNTPs.

EXAMPLES

Example 1

Protein Fragment Complementation by Incremental Truncation

Two overlapping fragments of the *E. coli* purN gene (which encodes glycinamide ribonucleotide formyltransferase) were cloned into compatible vectors pDIM-N2 and pDIM-C6. The N-terminus fragment (purN[1-144]) consists of the DNA coding for residues 1-144 and the C-terminus fragment (purN [63-212]) consists of the DNA coding for residues 63-212.

Phagemids pDIM-N2 and pDIM-C6 were constructed by a series of oligo replacements into vectors pMOpelB.H and pMOpelB.L designed for creating very large Fab antibody libraries. These antibody vectors were derived from pBP107 (Posner et al., *Gene* 128:111-117 (1993)) and pTC01 (Collet et al., *Proc. Natl. Acad. Sci. USA* 89:10026-10030 (1992)), respectively.

Two micrograms of PstI/XbaI-digested pDIM-N2 or SacI/XhoI-digested pDIM-C6 were equilibrated at 12° C. in 60 microliters of 66 millimolar Tris, pH 8.0/0.66 millimolar $MgCl_2$. At time zero, 200 units of exonuclease III were added. One-microliter samples were removed every 30 seconds thereafter for 30 minutes and added to a tube incubating at 4° C. containing 180 microliters of S1 nuclease buffer (41 millimolar K-acetate, pH 4.6/365 millimolar NaCl/1.4 millimolar $ZnSO_4$/6.8 percent glycerol), and 25 units of S1 nuclease.

After all samples were collected, the tube was incubated at room temperature for 30 minutes. Subsequently, 24 microliters of S1 stop buffer (0.3 molar Tris/50 millimolar EDTA) were added, and the tube was incubated at 72° C. for 20 minutes to fully inactivate S1 nuclease as well as Exo III. After an ethanol precipitation with ammonium acetate, the DNA was resuspended in 88 microliters of water and digested with either NsiI (pDIM-N2) or NcoI (PDIM-C6). After a second ethanol precipitation, the pDIM-C6 DNA was incubated with 2.5 units of the Klenow fragment (in 2 millimolar Tris, pH 8.0/10 millimolar $MgCl_2$ containing 0.125 millimolar each dATP, dCTP, dGTP, and dTTP) for 5 minutes at 37° C.

For pDIM-N2, the DNA was first incubated in the same buffer with the dNTPs for 3 minutes at 37° C. to use the Klenow fragment's 3'-to-5' exonuclease activity to blunt the 3' overhang left by NsiI digestion. Subsequently pDIM-N2 DNA was incubated with the dNTPs as above.

After heat inactivation of the Klenow fragment by incubation at 75° C. for 20 minutes, 400 microliters of ligase mix (50 millimolar Tris.HCl, pH 7.6/10 millimolar $MgCl_2$/1 millimolar ATP/5 percent PEG-800/1 millimolar DTT) containing 15 units of DNA ligase were added for unimolecular blunt end ligation overnight at room temperature. The DNA was concentrated by ethanol precipitation into 30 microliters of water and was electroporated into JS5 cells (Bio-Rad) by six electroporations of 5 microliters of DNA each. After recovery at 37° C. for one hour in 6 milliliters of SOB medium (2 percent Bacto-Tryptone/0.5 percent Bacto-Yeast extract/10 millimolar NaCl/2.5 millimolar KCl/10 millimolar $MgSO_4$) containing 2 percent glucose, the cells were plated onto a 243×243 millimeter TY medium plate (0.8 percent Bacto-Tryptone/0.5 percent Bacto-Yeast extract/0.5 percent NaCl/1.5 percent agar) containing 2 percent glucose and either ampicillin (100 micrograms/milliliter) or chloramphenicol (50 micrograms/milliliter). After growth overnight (about 16 hours) at 37° C., the library was recovered from the plate into 20 milliliters of 2×TY/2 percent glucose/15 percent glycerol, concentrated by centrifugation, and frozen in small aliquots.

The N-terminal and C-terminal truncation libraries were packaged into phage particles with the use of helper phage and infected into a 10 milliliter culture of exponentially growing *E. coli* strain TX680F' (constructed by mating TX680 with XL-1 blue) at a titer such that approximately 1-5 percent of the cells became infected with both plasmids. Infection proceeded for 30 minutes at 37° C. without shaking.

The cells were then centrifuged, washed once with 10 milliliters of selective medium (M9 salts, 0.2 percent glucose, 0.06 percent caseine, 2 micrograms per milliliter of thiamine, 40 micrograms per milliliter of kanamycin), and resuspended in 2 milliliters of selective media. The culture was shaken at 37° C. for 2 hours before plating dilutions on selective plates with 0.3 millimolar isopropyl β-D-thiogalactoside. Plates were incubated at 37° C. for up to 48 hours.

Randomly chosen colonies that appeared within 28 hours were restreaked on selective plates to affirm complementation and ensure isolation of a single positive. From these plates, positives were restreaked onto rich plates (TY) containing ampicillin and chloramphenicol. Colonies from the rich plates were tested for PurN recombination by a PCR screen by using primers for the beginning and end of the purN gene. The plasmid DNA from those positives that were not recombinants was isolated and transformed at very dilute concentrations into *E. coli* strain DH5α so that the two plasmids could be isolated and sequenced. The plasmid DNA from these DH5α transformants were retransformed back into the auxotroph (both separately and together) to confirm complementation resulted from PurN heterodimers. After complementation was confirmed, sequencing of the truncated genes was performed by the Nucleic Acid Facility at the Pennsylvania State University.

Cells from overnight (approximately 16 hours) cultures in LB media (supplemented with 2 percent glucose, 100 micrograms per milliliter of ampicillin, 50 micrograms per milliliter of chloramphenicol, and 12.5 micrograms per milliliter of tetracycline) were washed once in 5 volumes of minimal growth medium [M9 salts, 0.2 percent glucose, 2 micrograms per milliliter of thiamine, all 20 amino acids at recommended levels (Gerhardt, et al., *Methods for General and Molecular Bacteriology*, Am. Soc. Microbiol., Washington, D.C. (1994)), 40 micrograms per milliliter of kanamycin, 12.5 micrograms per milliliter of tetracycline, and 0.3 millimolar isopropyl β-D-thiogalactoside] and diluted 1,000-fold into 50 milliliters of minimal growth medium in 250 milliliter flasks. Cultures were shaken at 200 revolutions per minute at 37° C., and growth was monitored by removing 1 milliliter samples at various times and measuring the OD at 600 nanometers. Doubling time was calculated during early exponential phase ($OD_{600}$=0.02-0.10). Because the lag times for auxotrophic cells expressing either wild-type monomer PurN or the heterodimers were essentially identical (approximately 2.5 hours), the growth rates measured cannot have been the result of a recombination event.

Example 2

Incremental Truncation for the Creation of Hybrid Enzymes

Phagemids pDIM-N2 and pDIM-C6 are described elsewhere herein. Phagemid pDIM-C8 is identical to pDIM-C6 except for the substitution of a BglII site for the BamHI site and the substitution of a NsiI site for a PstI site 10 base pairs downstream from the SpeI site.

Incremental Truncation:

Incremental truncation was performed essentially as described above in Example 1, with the following modifications. Supercoiled pDIM-N2 and pDIM-C8 were linearized by digestion with XbaI/PstI and SacI/XhoI, respectively. The Exo III digestion was performed at 22° C. in 60 microliters of 66 millimolar Tris (pH 8.0), 0.66 millimolar $MgCl_2$, 100 millimolar NaCl. After inactivation of Exo III and S1 nuclease, the ethanol-precipitated DNA was resuspended in 70 microliters of water. After the addition of 10 microliters of 0.125 micromolar each dNTP, 2.5 units of Klenow fragment (in 2 millimolar Tris.HCl, 10 millimolar $MgCl_2$, pH 8.0) were added, and the mixture was incubated for 5 minutes at 37° C. followed by heat inactivation of Klenow fragment at 72° C. for 20 minutes.

The DNA was digested with NsiI (15 units) at 37° C. for 2 hours, and the desired fragments were isolated by gel electrophoresis using Elutrap® (Schleicher & Schuell; Keene, N.H.), combined, and concentrated by ethanol precipitation. Ligation was carried out at 15° C. overnight (approximately 16 hours) in a total volume of 20 microliters using 6 Weiss units of T4 DNA ligase. The ligated DNA was desalted by ethanol precipitation into 30 microliters of water and was electroporated into DH5α cells by six electroporations of 5 microliters DNA each or into DH5α-E (Life Technologies; Rockville, Md.) by two electroporations of 4 microliters each. Libraries were recovered and stored as described in Example 1.

Selection of Active Hybrids:

Plasmid DNA of the ITCHY and DNA shuffling libraries was transformed into TX680F', recovered, and frozen as described above. In a 250 microliter shake flask, 50 microliters of 2×TY/Amp/Kan/0.2 percent glucose were inoculated with 10 microliters of the frozen library (greater than 108 colony forming units) and grown at 37° C. until $OD_{600nm}$=0.2. Cells from 10 milliliters of culture were pelleted by centrifugation, washed once with 10 milliliters of selective medium, and resuspended in 2 milliliters of selective medium. After 2 hours of shaking at 37° C., approximately $2.5 \times 10^6$ colony forming units (rich medium) were plated onto selective plates containing 0.3 millimolar isopropylthiogalactoside. Plates were incubated at 37° C. for up to 48 hours. Randomly chosen colonies were processed and sequenced, and complementation was verified as described above.

Kinetic Characterization:

Kinetic characterization using GAR and fDDF were performed as described in Shim & Benkovic, *Biochemistry* 37:8776-8782 (1998). Wild-type *E. coli* PurN was prepared as described in Almassy et al., *Proc. Natl. Acad. Sci. USA* 89:6114-6118 (1992). The PurN-GART fusions were prepared by the same method using the vector isolated from the positive (pDIM-N2) and TX680F' cells. Fusion concentrations were estimated by densitometry of SDS-PAGE separation of the most active gel filtration fraction. Purified GARS-AIRS-GART was a gift from L. T. Gooljarsingh (The Pennsylvania State University, University Park, Pa.).

Example 3

Creation of a Circular Permuted Incremental Truncation Hybrid Library

Materials and Methods

All enzymes used were from New England Biolabs (Beverley, Mass.) unless otherwise indicated.

Figure 9:
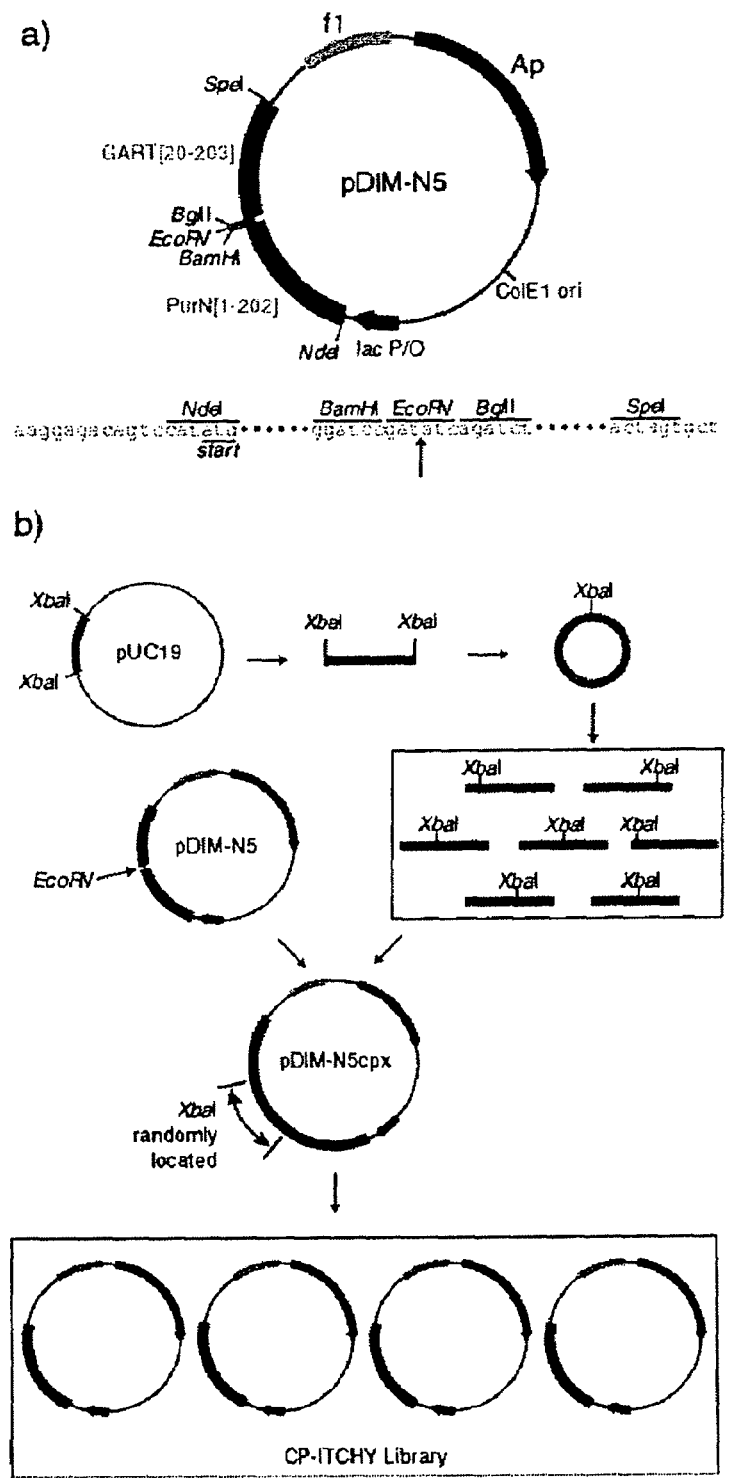
FIG. 9 (as FIGS. 9A and 9B) shows the creation of CP-ITCHY libraries.

Plasmid Constructs:

Phagemid pDIM-N5 was created by replacing the short BamHI-NsiI fragment of pDIM-N2 with an oligonucleotide as described in FIG. 9. Phagemid pDIM-N-5-PurN[1-202*]/GART[20-203] contains a fragment of the *E. coli* purN gene that encodes amino acid residues 1-202 (with the mutation D144A) between the NdeI and BamHI sites of pDIM-N5 and a fragment of the human GART gene that encodes amino acid residues 20-203 between the BglII and SpeI sites of pDIM-N5. The vector has a stop codon between codon 202 of purN and the BamHI site.

Creation of the Circularly Permuted Insert:

A 528 basepair fragment of the *E. coli* purK gene was amplified by PCR using oligos Xba-for

```
                                           (SEQ ID NO:1)
(5'-TTAGGCCGTCTAGAGCGTCAGGCAGGCGAACCG-3')
and Xba-528
                                           (SEQ ID NO:2)
(5'-GCGGAAAATCTAGACTGGTGCGCAAAATACCG-3')
``` such that it was flanked by XbaI sites (underlined). This fragment was digested with XbaI and cloned into the unique XbaI site of pUC19 to create pUC19-Xba528. Seventy micrograms of pCU19-Xba528 were digested with 1500 units XbaI and the shorter fragment isolated by gel electrophoresis using QIAEX® II (QIAGEN; Valenicia, Calif.). Six micrograms of this fragment were treated with 200 Weiss units T4 DNA Ligase in a total volume of 1.7 milliliters of ligase buffer (50 millimolar Tris-HCl (pH 7.5), 10 millimolar $MgCl_2$, 10 millimolar dithiothreitol, 1 millimolar ATP, 25 micrograms per milliliter bovine serum albumin) for 18 hours at 16° C. The ligation mixture was diluted with water up to 4 milliliters and concentrated approximately fifty-fold using Centricon-30™ spin columns (Millipore, Bedford, Mass.). The DNA was then digested with 600 units Exo III (Promega; Madison, Wis.) in Exo III buffer (66 millimolar Tris-HCl, pH 8, 0.66 millimolar $MgCl_2$) in a volume of 200 microliters for 30 minutes at 37° C. to remove any unligated linear DNA. Exo III was inactivated by incubation at 72° C. for 20 minutes. The circular DNA was desalted using QIAEX® II into a final volume of 50 microliters EB buffer (10 millimolar Tris-HCl, pH 8.5).

A series of test digestions was performed to determine the concentration of DNase I that provided the highest yield of linear product. The DNase I (RNase-free from Roche Molecular Biochemicals, Indianapolis, Ind.) was prepared by creating a working stock of 1 unit per microliter in 50 millimolar Tris-HCl, pH7.5 and 50 percent glycerol that was stored at −20° C. On the day of use, the working stock was diluted into 50 millimolar Tris-HCl (pH 7.5), 1 millimolar $MnCl_2$ and 50 micrograms per milliliter bovine serum albumin. For this study, 30 microliters of circular DNA were digested with 0.83 milliunits DNase I at 22° C. for 15 minutes in 50 millimolar Tris-HCl (pH 7.5) and 1 millimolar $MnCl_2$ in a volume of 400 microliters. The digestion was stopped by the addition of 20 microliters 50 millimolar EDTA, pH 8.0 and desalted using QIAquick™ columns (QIAGEN) into 50 microliters of EB buffer. The linearized DNA was repaired using 3 units T4 DNA polymerase and 6 Weiss units T4 DNA ligase in ligase buffer that included 125 micromolar each dNTP. The repaired, linearized DNA (i.e., the circularly permuted insert) was isolated by agarose gel electrophoresis using QIAEX® II into 20 microliters of EB buffer.

The vector was prepared by digesting 10 micrograms of pDIM-N-5-PurN[1-202*]/GART[20-203] with 50 units of EcoRV in 100 microliters for 2.5 hours. Subsequently, 90 microliters of water, 10 microliters CIAP buffer (500 millimolar Tris-HCl (pH 9.3), 10 millimolar $MgCl_2$, 1 millimolar $ZnCl_2$, 10 millimolar spermidine) and 7 units of calf intestinal alkaline phosphatase (Promega) were added and the solution incubated for an additional 1 hour at 37° C. To inactivate the alkaline phosphatase, 2 microliters of 500 millimolar EDTA, pH 8.0 was added and the DNA incubated at 72° C. for 15 minutes. The DNA was purified by agarose gel electrophoresis using QIAEX® II into a total of 50 microliters of EB buffer.

One hundred nanograms of EcoRV-treated, dephosphorylated vector were ligated to 10 microliters of circularly permuted insert with 30 Weiss units of T4 DNA ligase in a volume of 15 microliters at 22° C. for about 20 hours. Eight electroporations of 1 microliter ligation mix into 50 microliters of DH5α-E electrocompetent cells (rated at approximately $10^{10}$ transformants per microgram of DNA) resulted in a library of $1.1 \times 10^6$ transformants on a 243×243 mm plate. The library was recovered and stored as previously described. Ostermeier, M. et al., *Proc. Natl. Acad. Sci. USA* 96:3562-3567 (1999).

PCR Characterization of Circularly Permuted Insert:

Individual colonies resulting from plating a dilution of the frozen library were analyzed by PCR to determine the location of the XbaI site in individual members of the library. Because it is unknown for any given colony which orientation the circularly permuted insert exists, three oligos were used in the PCR reaction: Xba-for, Xba-528 and PurN-for

```
                                    (SEQ ID NO:3)
(5'-GATATACATATGAATATTGTGGTGCTTATTTCC-3'),
``` an oligo that annealed to the beginning of the purN gene. Depending on which orientation the circularly permuted insert was ligated, either (PurN-for and Xba-528) or (PurN-for and Xba-for) would produce an exponential amplification. The size of the PCR product was determined by agarose gel electrophoresis and the location of the XbaI site was then determined by subtracting the size of purN[1-202*].

Incremental Truncation:

A plasmid prep (QIAGEN® Midiprep; QIAGEN) on 40 percent of the frozen library yielded 54 micrograms of supercoiled plasmid. The plasmid DNA (20 micrograms) was digested with 40 units of XbaI for 1.5 hours at 37° C. The linearized vector was isolated from uncut vector and vector not containing the circularly permuted insert by agarose gel electrophoresis using QIAEX® II.

Exo III digestion was performed on 4 micrograms of linearized vector at 22° C. in 120 microliters of 66 millimolar Tris (pH 8.0)/0.66 millimolar $MgCl_2$/50 millimolar NaCl using 800 units of Exo III. Twenty-four microliter aliquots were removed at 24, 25, 26, 27 and 28 minutes and added to 72 microliters of 40.5 millimolar potassium acetate (pH 4.6), 338 millimolar NaCl, 1.35 millimolar $ZnSO_4$, 6.76 percent glycerol at 4° C. to quench the digestion. After all the samples had been quenched, 0.5 milliliters of QIAquick™ buffer PB (QIAGEN) were added and the DNA purified using the QIAquick™ protocol with one modification: after the addition of the wash PE buffer the samples were incubated for 5 minutes at room temperature before spinning to insure removal of any salt.

The DNA was eluted from the QIAquick™ column using 47 microliters of EB buffer. To this eluate, 5 microliters of 10× mung bean buffer (500 millimolar sodium acetate (pH 5.0), 300 millimolar NaCl, 10 millimolar $ZnCl_2$) and 0.4 units mung bean nuclease were added and the solution incubated at 30° C. for 30 minutes. Next, 0.25 milliliters of QIAquick™ buffer PB (QIAGEN) were added and the DNA purified using the QIAquick™ protocol with the modification listed above.

The DNA was eluted from the QIAquick™ column using 47 microliters of buffer EB. To this eluate, 5 microliters of dNTP mix (0.125 millimolar each dNTP) and 5 microliters of 10× EcoPol buffer (100 millimolar Tris-HCl (pH 7.5), 50 millimolar. $MgCl_2$, 75 millimolar dithiothreitol) were added and the solution equilibrated to 37° C. Next, one unit of Klenow DNA polymerase was added. Following a five-minute incubation at 37° C., the Klenow-containing composition was heat inactivated at 75° C. for 20 minutes. To this solution was added 98.7 microliters of water, 20 microliters of 10× ligation buffer, 20 microliters of 50 percent PEG and 1.33 microliters of T4 DNA ligase (8 Weiss units) and the solution was incubated at room temperature overnight (about 16 hours).

The DNA was concentrated by ethanol precipitation (with ammonium acetate as salt) into 10 microliters of water. A single electroporation of 3 microliters of DNA into 50 microliters of TX680F' electrocompetent cells (rated at $1 \times 10^8$ transformants per microgram pUC19) resulted in a library of approximately $1 \times 10^6$ for each time point.

Selection of Active Fusions:

Active PurN-GART fusions were identified by complementation of a GAR transformylase auxotrophic *E. coli* strain (TX680F') as previously described above.

Results

The mathematical description of the basis of circularly permuted ITCHY (CP-ITCHY) is shown in FIG. 8. In this method, both gene fragments to be truncated are located on a single vector (FIG. 9) between which is inserted a piece of DNA that has a randomly located unique restriction site (XbaI) and is preferably equal in length to the length of overlap between the two gene fragments. This library of constructs containing a randomly located restriction enzyme site is constructed by a method involving the circular permutation of a piece of DNA (FIG. 9B). In other methods of the invention, variation in truncation length is created by truncating for various lengths of time from a fixed point on the DNA. In this method, variation in truncation length is created by truncating for one length of time from various points on the DNA.

Description of Model System:

As shown elsewhere, methods of the invention can be used to identify active fusions between an N-terminal fragment of PurN (*E. coli* glycinamide ribonucleotide formyltransferase) and a C-terminal fragment of GART (human glycinamide ribonucleotide formyltransferase). Ostermeier, M., et al., *Nature Biotech.* 17:1205-1209 (1999). Although the study was designed to search for active hybrids fused anywhere between amino acid residues 54 and 144, all of the active hybrids were only found to be fused between amino acid residues 100 and 144, almost all of them fused exactly where the sequences align.

This model system was used to test a method of making a plurality of circularly permuted incrementally truncated hybrids (sometimes referred to herein as CP-ITCHY) and at the same time expand the range of search to between amino acid residues 20 and 144. An expanded range of incremental truncation was sought to extend from 270 basepairs to over 500 basepairs. However, fragments of PurN larger than PurN [1-144] may be active by themselves. In order to expand the range of truncation, without having fusions between PurN and GART active solely due to PurN residues, fragments of PurN were used in which residue 144 had been mutated from aspartate to alanine, a mutation that inactivates PurN. Shim, J. H. and Benkovic, S. J. *Biochem.* 38:10024-10031 (1999). Thus the fragments used were GART [20-203] and PurN[1-202*], with the star symbolizing the mutation. This gives a range of overlap between the two fragments of 182 amino acid residues (546 basepairs), almost the entire length of the two genes. However, because of the D144A mutation in PurN [1-202*], active fusions between 145 and 202 were not expected to be found.

Library of Circular Permutation Hybrids:

Fragments purN[1-202*] and GART[20-203] were cloned into phagemid pDIM-N5 as shown in FIG. 9A. This phagemid was linearized by digestion between the two gene fragments with EcoRV, treated with alkaline phosphatase and purified by agarose gel electrophoresis in preparation for cloning in the circularly permuted insert.

A fragment of the purK gene was amplified such that it was flanked with XbaI sites. The length of the purK fragment was such that once it was circularly permuted and cloned into pDIM-N5, the distance between the end of the end of purN [1-202*] and the beginning of GART[20-203] would be equal to the overlap between the purN[1-202*] and GART[20-203] in a sequence alignment.

Although in principal the PCR product can be used directly in the circular permutation scheme, better results were obtained by first cloning it into the XbaI site of pUC19, digesting it out with XbaI and isolating the fragment by agarose gel electrophoresis. The fragment of purK with XbaI overhangs was cyclized by ligation under dilute concentrations of DNA, so that the major product was closed, circular DNA.

Because a small amount of linear starting material was sometimes found after cyclization, the ligase-treated DNA was incubated with Exo III to remove the linear DNA, which would unproductively bias the incremental truncation library. Next, the circular DNA was digested with the amount of DNase I that gave the highest yield of linear DNA (e.g., the amount of DNase I necessary to produce, on average, one double-stranded break in the circular DNA). This DNase I-digested DNA was treated with T4 DNA ligase and T4 DNA polymerase in the presence of dNTPs to repair gaps and nicks in the linearized product and to produce blunt ends. This blunt-end, circularly permuted DNA was inserted into pDIM-N5 that had been treated with EcoRV and alkaline phosphatase by ligation at 22° C.

Electroporation into DH5α-E resulted in a library of $1.1 \times 10^6$ transformants, making it all but certain that the approximately 500 possible circular permutations were present. To confirm a random distribution of XbaI sites in the library, PCR was performed on randomly selected colonies. As expected, the location of the XbaI site was essentially random.

General Improvements to Incremental Truncation:

Two changes to the earlier examples are noted. First, mung bean nuclease was used instead of S1 nuclease for removing the single stranded tail after Exo III digestion. It has been found that S1 nuclease periodically would fail to remove the single stranded tail from all of the DNA molecules and this primarily accounted for the bias towards shorter truncations noted previously. It appears that this occasional failure correlated most with the DNA to be truncated, and S1 nuclease is suspected to be sensitive to some impurity in plasmid DNA preps.

The second improvement was replacing the heat inactivation and ethanol precipitation with a DNA affinity column (QIAquick™) to purify the DNA away from Exo III and the single stranded nuclease. This significantly improved the yield and quality of the truncated DNA.

CP-ITCHY Library:

Plasmid from the circular permutation hybrid library was digested with XbaI and purified by agarose gel electrophoresis in preparation for truncation. Using control digestions on this DNA, it was found that under the conditions used (4 micrograms of DNA in 120 microliters of 66 millimolar Tris (pH 8.0)/0.66 millimolar $MgCl_2$/50 millimolar NaCl with 800 units of Exo III at 22° C.) the rate of Exo III digestion was approximately 21 basepairs per minute in each direction. Thus, to digest 546 basepairs in each direction requires a digestion time of 26 minutes.

The XbaI-digested DNA was digested with Exo III for 24, 25, 26, 27 or 28 minutes before quenching in a high salt, low pH buffer. These five libraries are subsequently referred to as CP-24, CP-25, etc. The DNA was desalted and purified away from the Exo III using a QIAquick™ affinity column. After treatment with mung bean nuclease to remove the single stranded tail, the DNA was treated with the Klenow fragment to assure blunt ends. Ligation at 22° C. under dilute conditions circularized the truncated DNA library.

The DNA was concentrated by ethanol precipitation into 10 microliters and 3 microliters of this was electroporated into 50 microliters of electrocompetent TX680F' cells (determined to transform with pUC19 at $1 \times 10^8$ transformants per microgram). The size of the five libraries (the number of transformants) ranged from $9 \times 10^5$ to $1.1 \times 10^6$.

The size distribution in the five libraries was determined by agarose gel electrophoresis of PCR reactions on 55 randomly selected members of the five libraries using PurN forward and GART reverse primers. This method creates a library biased towards those fusions that are about the same size as the original genes, whereas other methods of the invention provide a more flat distribution.

Selection of Active Fusions:

Active members of the five libraries were identified by complementation of an *E. coli* auxotroph grown at 37° C. as previously described. Ostermeier, M. et al., *Nature Biotech.* 17:1205-1209 (1999). As expected, the highest frequency of active fusions was found in CP-26. However, owing to the size of the standard deviation in truncation length, which increases linearly with the length of truncation as 22 basepairs per 100 basepairs truncated (Hoheisel, J. D. *Anal. Biochem.* 209:238-246 (1993)), active fusions were found in the other four libraries as well. The frequency of fusions in CP-26 is approximately four-fold higher than that which would be expected in a method of making a plurality of incrementally truncated hybrid genes. The frequency of positives expected in such a so-called TV-ITCHY library over the same size range was estimated by taking the frequency in a smaller library where truncations occurred over 270 basepairs (Ostermeier, M. et al., *Nature Biotech.* 17:1205-1209 (1999)) and, knowing that no new fusions are found outside the range of this library when the truncation range is 546 basepairs (see below), dividing by the ratio of the theoretical library sizes for truncations of 546 and 270 basepairs ($546^2/270^2$).

Twenty random active fusions were sequenced. Like the 20 randomly selected active members of TV-ITCHY library IT-B (which identified eleven different DNA sequences and seven different proteins) (Ostermeier, M. et al., *Nature Biotech.* 17:1205-1209 (1999)), CP-ITCHY identifies a variety of different fusion points (ten different DNA sequences and six different proteins) at homologous and non-homologous locations. Three of the six proteins identified by CP-ITCHY are newly identified active fusions.

Temperature Sensitive Fusions:

CP-ITCHY libraries CP-24 and CP-27 were also tested for complementation of the auxotroph at 22° C. The frequency of positives at 22° C. was found to be 8.0- and 5.4-fold higher, respectively, than the frequency of positives at 37° C. Of ten randomly chosen positives of CP-24 selected at 22° C., five were found to be unable to grow at 37° C. The gene fusions from all ten positives were sequenced. The five temperature sensitive fusions were fused in a region between amino acid residues 80 and 90, a region where no active fusions had previously been identified. The five non-temperature sensitive fusions were fused in regions previously identified by selection at 37° C.

Example 4

Creation of a Shuffled Incrementally Truncated Gene Library

A. Overview:

The *E. coli* PurN and FMT proteins are both formyltransferases that transfer the formyl group from formyltetrahydrofolate to their substrate. The substrate for PurN is glycinamide ribonucleotide and the substrate for FMT is methionyl-tRNA. The N-terminal domain of FMT has been shown to be structurally homologous to PurN and both PurN and FMT contain identical key active site residues (N106, H108 and D144 for PurN and N109, H111 and D147 for FMT). This is suggestive of a common ancestral protein. However, the DNA sequence homology between the two is very low (approximately 30-35 percent, depending on how the alignment is performed), too low to perform in vitro recombination between the two genes. PurN and FMT were used to create a shuffled incrementally truncated hybrid gene (sometimes referred to herein as SCRATCHY) library of PurN-FMT hybrids with more than one crossover.

Figure 10:
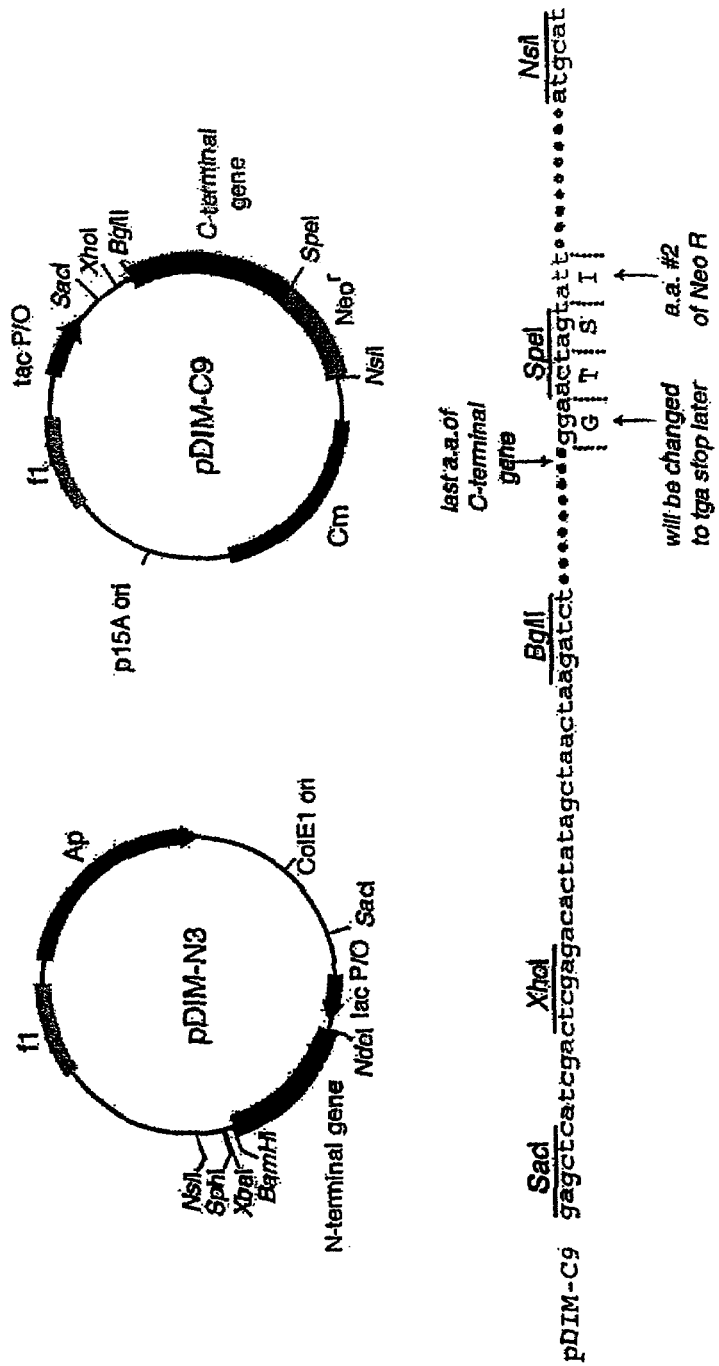
FIG. 10 is a depiction of exemplary vectors used for the creation of SCRATCHY libraries, as well as includes the following DNA sequences: SEQ ID NO:9 gagctcatcgactcgagacactatagctaactaagatct, SEQ ID NO:10 ggaactagtatt and SEQ ID NO:11 atgcat.

B. Creating the ITCHY Libraries:

Vectors for creating SCRATCHY libraries are shown in FIG. 10. Two ITCHY libraries were made between fragments of purN and FMT by the TV-ITCHY method. In the first library (N-F), the starting N-terminal gene fragment was PurN[1-164] and the starting C-terminal gene fragment was FMT[89-214]. In the second library (F-N), the starting N-terminal gene fragment was FMT[1-167] and the starting C-terminal gene fragment was PurN[86-212]. In both libraries the PurN fragment contained the following point mutations in the three key active site residues: N106W, H108R and D144L. For diagnostic purposes, a silent mutation was made in codon 107 such that a BamHI restriction site was created within codons 106-108. The DNA homology in the region of overlap between these fragments is 34 percent. Both N-F and F-N ITCHY libraries were designed such that between 0 and 300 bases were deleted from each of the fragments listed above. Based on the number of transformants, library N-F had $3.7 \times 10^5$ members and library F-N had $5.5 \times 10^5$ members.

C. Selection for In-Frame Fusions:

In each of the libraries, the C-terminal gene fragment was fused in-frame to the neomycin resistance gene. Thus, each ITCHY library member has a fusion of a fragment of PurN and a fragment of FMT, to the C-terminus of which is fused the neomycin resistance gene. Only those fusions of PurN and FMT fragments that are in-frame will make a tri-fusion protein containing the neomycin resistance protein. Thus, in-frame fusions of PurN and FMT fragments can be selected for by plating the library on kanamycin. This was performed by plating $2.5 \times 10^7$ colony forming units of libraries N-F and F-N on 243×243 mm TY plate containing 20 micrograms per milliliter of kanamycin. These kanamycin-selected libraries are referred to as N-F-k and F-N-k respectively. The lawn of colonies was recovered from these plates and sequencing showed that 14 of 15 randomly chosen library members were fused in-frame. Combining this result with results from two other PurN-FMT libraries, in which 8 of 8 members were in-frame, demonstrates that the method enriches the percentage of in-frame fusions in the library from 33 percent to 96 percent. The value of such enrichment is clear when one compares a hypothetical SCRATCHY library member with four ITCHY crossovers from shuffling of the kanamycin-selected library to that of the unselected library. The former has an $(0.96)^4 = 85$ percent, and the latter has a $(0.33)^4 = 1$ percent, chance of being entirely in-frame. The N-F-k and F-N-k libraries exhibit a very diverse set of fusion points.

D. Selection for Desired Size Fusions:

After selection for in-frame fusions, the libraries were selected for size as follows. Plasmid DNA from N-F-k and F-N-k was digested with SacI and SpeI. DNA of the desired size (i.e., such that the fusion of purN and FMT are approximately the same size as the PurN gene) was isolated by agarose gel electrophoresis of four micrograms of each digested plasmid. Gel electrophoresis was performed on a 15×25 centimeter gel at low voltage for 8 hours to maximize separation. It was estimated based on the size of the gel slice that the DNA recovered from the gel contained a fusion of PurN and FMT of 636 basepairs (N-F-k) or 648 (F-N-k) plus or minus 10-15 basepairs.

E. In Vitro Recombination:

To obtain enough material to perform in vitro recombination and to reintroduce a stop codon at the C-terminus of the PurN-FMT and FMT-PurN fusions, PCR was performed on the DNA recovered from the agarose gel. A 1:1 mix of Taq and Pfu polymerases was used in this and subsequent PCR reactions to control the number of point mutations to approximately one per gene. The amplified DNA was recombined in vitro using an established protocol (Zhao, H. and Arnold, F. H. *Nucleic Acids Res.* 25:1307-1308 (1997)) using four different DNaseI dilutions and with an annealing temperature of 50° C. during the reassembly step. For the amplification with outside primers, the DNA was fixed at the 5' and 3' ends of the shuffled gene as from purN. Thus, the libraries predominantly consist of genes with 0, 2, 4, 6, etc., crossovers. The shuffled gene was cloned between the NdeI and SpeI sites of vector pDIM-N5 to create four libraries, one for each of the four DNaseI digestions. These library sizes varied from $2.0 \times 10^6$ to $2.8 \times 10^6$.

Twenty random members from one of the libraries were sequenced. Fifteen had no crossovers (reassembled PurN with the active site mutations) and one had a single crossover (i.e. it was an FMT-PurN fusion). Four of the 20 members had two crossovers indicating that this library had approximately 400,000 members in which a piece of FMT had been inserted within PurN. The size of the FMT piece in these four ranged from 36 to 160 basepairs. Each of the eight crossovers were unique and were in regions of low homology, making it most probable that they resulted from being present in the original ITCHY libraries and not from recombination. The crossovers showed a range of size selection that was between 8 basepairs larger and 9 basepairs smaller than the desired size. The number of point mutations per gene ranged between zero and two and averaged 0.8 per gene.

Example 5

Creation of an Analog-Containing Incrementally Truncated Hybrid Gene Library

Materials and Methods

All enzymes used were purchased from New England Biolabs (Beverly, Mass.) unless otherwise indicated. The α-phosphorothioate nucleotides (racemic mixtures, as well as S-stereoisomers) used in the studies had previously been synthesized (Chen and Benkovic, Nucl. Acids Res. 11:3737-3751 (1983)). Racemic mixtures of α-S dNTPs are also commercially available from Promega (Madison, Wis.) and Amersham/Pharmacia (Piscataway, N.J.). DNA samples were purified by using the QIAquick® Gel and PCR purification kit (QIAGEN; Valencia, Calif.). Where indicated, reactions were quenched by addition of PB buffer, supplied with the QIAquick® PCR purification kit. The DNA was eluted from the spin columns, using 50 microliters of the provided EB-buffer (10 millimolar Tris (pH 8.5)).

Figure 11:
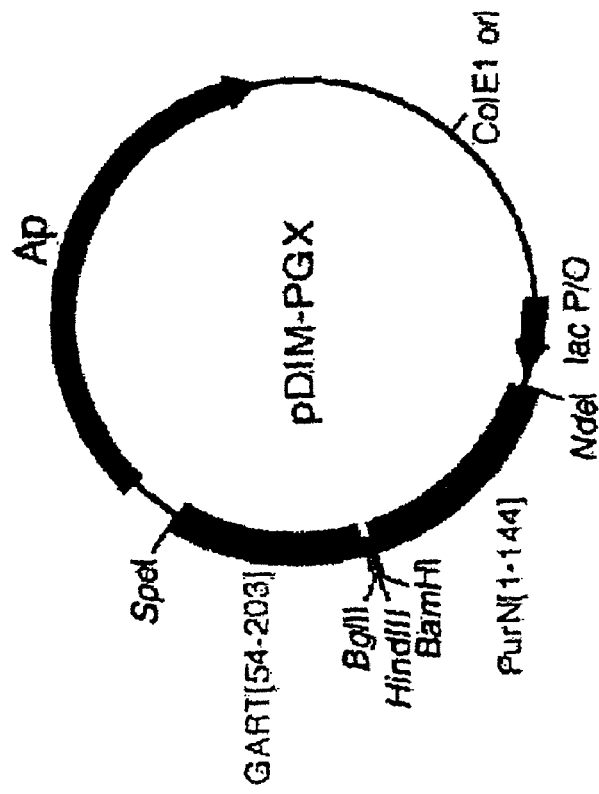
FIG. 11 is a depiction of an exemplary vector used for the creation of a THIO-ITCHY library, as well as includes the following DNA sequences: SEQ ID NO:6 aaggagacagtccatatg, SEQ ID NO:12 ggatccgatatctagaagcttactgcagcgctcgagatatcagatct, and SEQ ID NO:13 actagtgctacc.

Plasmid Construction:

Plasmid pDIM-PGX (FIG. 11) was constructed from pDIM-N2(PurN[1-144]). Initially, the f1 region in pDIM-N2 (PurN[1-144]) was removed by restriction digest with KpnI and NaeI. The overhangs were filled in by Klenow treatment and the plasmid was cyclized, generating pDIM-N2(Δf1, PurN[1-144]). Next, the human GAR transformylase fragment [54-203] was prepared by PCR, carrying a 28-nucleotide linker region as a 5'-overhang, flanked by BamHI and BglII sites (FIG. 11). Upon digestion with BamHI/SpeI, the hGART fragment was ligated into pDIM-N2(Δf1, PurN[1-144]) and transformed into E. coli DH5α-E (Gibco-Life Technologies; Rockville, Md.). The resulting plasmid pDIM-PGX was isolated by large-scale plasmid prep (QIAGEN; Valencia, Calif.) and characterized by restriction analysis and DNA sequencing. Twenty micrograms of PDIM-PGX in 200 microliters of NEB-buffer #2 were linearized by restriction digest with HindIII (60 units) and purified by agarose gel electrophoresis.

DNA Spiking by Exonuclease/Klenow Treatment:

Three micrograms of linearized DNA were mixed with 6 microliters of exo III buffer (10×; Promega) and the volume adjusted to 60 microliters with water. The solution was pre-incubated for 15 minutes at 22° C., followed by addition of exonuclease III (260 units; Promega) and incubation at room temperature for 6 minutes. The average cutback rate under the described conditions was 50 bases/minute. The reaction was quenched with EDTA (1 microliter of 0.5 molar stock, pH 8) and the DNA QIAquick®-purified.

Resynthesis of the complementary DNA strands of the exonuclease-treated plasmid (50 microliters) was performed by incubation with Klenow fragment (exo$^-$) (3.75 units) in Tris-HCl (10 millimolar, pH7.5), MgCl$_2$ (5 millimolar), containing dNTPs (199 micromolar each) and αS-dNTPs (5 micromolar each; either S-isomer or racemic mixture) in a final volume of 150 microliters for 10 minutes at 37° C. The reaction mixture was quenched by addition of PB-buffer and the DNA QIAquick®-purified.

DNA Spiking by PCR:

α-Phosphorothioate nucleotides were incorporated directly during PCR amplification of the linearized pDIM-PGX. Ten nanograms of linearized plasmid were amplified with primers A:

(SEQ ID NO: 4)
(5'-TCCGGAGCTTCTAGATATCGGATCCTTAGTCC-3')
and

B:
(SEQ ID NO:5)
(5'-AGGCCTCTGCAGCGCTCGAGATATCAG-3')

(1 micromolar each) in 50 microliters of reaction mixture (Taq DNA polymerase buffer (Promega), supplemented with MgCl$_2$ (1 millimolar), dNTPs (180 micromolar each), αS-dNTPs (20 micromolar each), and 2.5 units Taq DNA polymerase (Promega)). PCR program: 5 minutes, 94° C.; followed by 30 cycles of 30 seconds, 94° C.; 30 seconds, 56° C.; 4 minutes and 30 seconds, 72° C.; followed by 10 minutes, 72° C. After purification with the QIAquick® kit, the amount of DNA was quantified by OD$_{260}$ for adjustment of the amount of exonuclease in the following step.

Creation of an Incremental Truncation Library:

The solution of spike DNA (50 microliters) from either protocol (PCR amplification or Exonuclease/Klenow treatment) was mixed with exonuclease III (120 units per microgram of 5'-end DNA; Promega) in the manufacturer's buffer (5.5 microliters, 10×; Promega) and incubated for 30 minutes at 37° C. After quenching the reaction with PB-buffer and QIAquick®-purification of the DNA, the single-stranded 5'-overhang was removed upon incubation with mung bean nuclease (2.3 units per microgram of DNA) in the manufacturer's buffer (30 minutes at 30° C.). The DNA was again QIAquick®-purified.

To improve the ligation efficiency, the plasmid library was blunt-ended with Klenow-fragment (4.5 units) in 6 microliters of Klenow buffer (Tris-HCl (100 millimolar, pH7.5), MgCl$_2$ (50 millimolar)) and dNTPs (final concentration of 140 micromolar per nucleotide) for 10 minutes at 37° C. The DNA was QIAquick®-purified.

In the final step, the plasmid library was cyclized by intramolecular ligation using T4 DNA ligase (24 units; Promega) in the manufacturer's buffer and 36 microliters of PEG (50 percent) (final volume: 400 microliters) overnight (approximately 16 hours) at 4° C. Prior to transformation into E. coli DH5α-E (Life Technologies, Rockville Md.; approximately $10^{10}$ transformants per microgram of DNA), the DNA was concentrated and desalted by using QIAquick® spin columns.

Selection of the THIO-ITCHY Libraries:

The incremental truncation library in DH5α-E was recovered and stored as described elsewhere herein. Following transformation into the auxotrophic E. coli strain TX680F', selection of active hybrids was carried out as described elsewhere herein.

Results

The creation of a nucleotide analog-containing incrementally truncated hybrid gene library was shown using the N-terminal gene fragment of E. coli glycinamide ribonucleotide transformylase (PurN [1-144]) and the C-terminal portion of the human glycinamide ribonucleotide transformylase (hGART [54-203]). Both enzymes catalyze the transfer of a formyl-group in the de-novo purine biosynthesis pathway. Despite their high overall structure homology, the two sequences share only 50 percent identity on the DNA level.

Creation of a THIO-ITCHY Library:

The use of α-thiophosphate nucleotides introduces several changes in the design of the vector containing the parental gene fragments. For example, the two genes are cloned in series within the same vector, rather than on two separate plasmids as in other embodiments of the invention (FIG. 11). This change permits the simultaneous truncation of both gene fragments, because fragment size-distribution of the truncation library is no longer dependent on the length or time interval of exonuclease digestion. Furthermore, the requirement for multiple, strategically placed restriction sites has been eliminated. Only a single unique cleavage site between the two gene fragments, such as the cloning site(s) of the target DNA, is required. Consequently the single-vector design simplifies the library construction in the final step of the protocol, allowing a single intramolecular ligation to recircularize the incremental truncation library.

As described, the THIO-ITCHY protocol consists of the following basic steps. The method starts with the linearization of the parental vector, using the unique restriction between the parental gene fragments. Gel-purification of the digestion product was found preferable to remove trace amounts of incompletely digested vector which otherwise gets carried through the remaining protocol and upon transformation leads to a bias in the library.

The next step involves the random incorporation of nucleotide analogs such as phosphorothioate-containing analogs into a target nucleic acid sequence. Nucleotide analogs can be incorporated into a target sequence using, for example, primer extension (sometimes referred to herein as Exonuclease/Klenow treatment) or PCR amplification.

Incorporation of Nucleotide Analogs by Primer Extension

Using exonuclease III, the two ends of the linearized plasmid, encoding the overlapping region between amino acid position 54 and 144 (270 basepairs) of PurN and hGART, were converted into single-stranded DNA. Exonuclease III, under carefully chosen reaction conditions, allows the controlled 3' to 5' hydrolysis of double stranded-DNA. At 22° C. in low salt buffer, the enzyme hydrolyzes approximately 50 basepairs per minute. The hydrolysis was quenched efficiently upon addition of EDTA. The application of QIAquick® spin columns to purify the DNA intermediate from protein and EDTA proved simple and very efficient.

The single-stranded DNA portion then served as template for the polymerase-catalyzed resynthesis of the complementary DNA strand. Using a mixture of the four standard dNTPs, spiked with small amounts of dNTP analogs such as αS-dNTPs, leads to the random incorporation of the nucleotide analogs over the entire stretch of the resynthesized DNA. Several DNA polymerases including Klenow fragment, T4 DNA polymerase, Taq DNA polymerase, Vent™ DNA polymerase, and Pfu DNA polymerase, have been shown to successfully utilize thiophosphate analogs during template-directed DNA synthesis (Nakamaye et al., Nucl. Acids Res. 16:9947-9959 (1988); Burgers and Epstein, J. Biol. Chem. 254:6889-6893 (1979)). However, none of the 3'-5' exonuclease activities of Klenow, T4, Vent™, and Pfu DNA polymerase is capable of hydrolyzing the thiophosphate linkage. Idling, taking place during the primer extension reaction as a result of the polymerase's exonuclease activity, would lead to accumulation of thiophosphates at the 3'-ends of the resynthesized strands, biasing the resulting library towards full-length fragment sizes. Exonuclease-deficient variants of these polymerases are therefore preferentially employed during the synthesis of the complementary strand.

Another important consideration during the fill-in reaction is the ratio between dNTPs and dNTP analogs, ultimately responsible for the diversity of the incremental truncation library. In theory, incorporation of a single dNMP analog over the length of the single-stranded DNA segment is desirable. In mathematical terms, the αS-dNTP to dNTP concentration ratio is inversely proportional to the length of the single-stranded DNA segment X scaled by a correction factor δ (see equation elsewhere herein). The correction factor represents the relative incorporation rates of dNTPs and αS-dNTPs. To a first approximation, the comparable incorporation efficiency of phosphorothioates versus natural nucleotides by E. coli DNA polymerase I and Taq DNA polymerase indicates no apparent discrimination (δ=1).

However, earlier studies showed that only the S-isomeric form of αS-dNTPs is utilized by DNA polymerases while the R-isomer acts as a mediocre, competitive inhibitor of the enzyme. Burgers and Epstein, J. Biol. Chem. 254:6889-6893 (1979). The lower overall efficiency of incorporation of phosphorothioate nucleotides by DNA polymerases in comparison to natural dNTPs must therefore be considered. This, as well as other unspecific effects have lead to an experimentally determined correction factor (δ=7.5) for Klenow fragment (exo⁻).

Incorporation of Nucleotide Analogs by PCR Amplification

Alternatively, introduction of nucleotide analogs by PCR amplification of the entire vector sequence has also been shown. While following the same guidelines for dNTP/αS-dNTP ratios and polymerases as described elsewhere herein for primer extension, PCR amplification requires only nanogram quantities of the initial construct and requires less hands-on time.

The size of the plasmid and the error frequency of the utilized DNA polymerase are also factors to be considered. Although random mutagenesis in the target DNA may be desirable, the approach inevitably introduces point mutations over the entire length of the plasmid that could disrupt or otherwise modulate other essential functions of the plasmid. Consequently, subcloning of the truncation library into a separate expression system can be performed, especially for larger constructs or under deliberately chosen highly mutagenic conditions.

Taq DNA polymerase, which has the lowest known error frequency of commercially available exonuclease-deficient DNA polymerases, was utilized to amplify and spike the linearized pDIM-PGX. The observed error frequency was $5 \times 10^{-4}$, based on sequencing data from functional hybrids.

Creating the Truncation Libraries from Nucleotide-Analog Spiked DNA

The DNA into which nucleotide analogs are incorporated is then incubated a second time with exonuclease III under conditions of maximum activity (approximately 450 basepairs per minute). Upon incubation with nucleases such as exonuclease III, only the randomly incorporated thiophosphate internucleotide linkages halt the degradation and protect the remaining plasmid from further hydrolysis. In control experiments, plasmid DNA containing only standard nucleotides was removed with great than 99 percent efficiency, based on the number of colonies formed upon ligation and transformation of these samples.

The single-stranded 5'-overhang that remains after exonuclease treatment was removed upon incubation with mung bean nuclease. The use of mung bean nuclease has proven very efficient and reliable, in contrast to initial studies with S1 nuclease (which gave inconsistent data). Although direct ligation of the mung bean-treated DNA was successfully performed, the additional blunt-ending step by Klenow treatment increased the number of transformants seven-fold.

Following the described protocol, a THIO-ITCHY library of PurN/hGART hybrid enzymes was generated, consisting of approximately $2-8 \times 10^5$ independent members. PCR analysis of the gene fusion product from randomly chosen library members indicated a linear size distribution over the expected range of truncation. In addition, the distribution of crossovers between the parental gene fragments, as well as the fragments size variation in the naïve library, were investigated by DNA sequencing of several plasmids from randomly chosen colonies. Their PurN/hGART fragment sizes and crossover points were established and plotted. Seven of the characterized sequences were found to be located in the desired sequence space between amino acid residue 54 and 144 while two library members were within the range of the standard deviation of the initial exonuclease digestion. Two samples were found outside the expected sequence space. The random distribution over the sampled sequence space indicates no apparent bias towards particular regions within the gene fragments, and most important, towards constructs composed of equal sized fragments. Such would be indicative for carried-over plasmid from the initial exonuclease treatment as a result of the synchronized hydrolysis of both 5'-ends by exonuclease. The data show that the random incorporation of nucleotide analogs, followed by the exonuclease step, results in a random fragment size recombination between the two genes.

Selection of Functional Hybrid Enzymes

For the selection of catalytically active hybrid enzymes, the plasmid library was recovered and transformed into the auxotroph *E. coli* strain TX680F'. Upon plating the transformants on minimum plates, only those bacteria grow whose expressed hybrid enzymes are capable of complementing the disrupted host-GAR transformylase. Selection was performed by incubating the plates at 37° C., as well as under less stringent selection conditions at room temperature. The lower incubation temperature yielded approximately four times the number of colonies found at 37° C. Although the majority of the constructs from the room temperature plate also grow at 37° C., additional temperature-sensitive hybrid enzymes were found. As described elsewhere herein, the fusion points of the temperature-sensitive hybrids were exclusively located in the region between amino acid 80 and 100. Furthermore, sequence analysis of the naive libraries identified an in-frame fusion construct (PurN 1-72/GART 73-203) in the lower overlapping region (amino acid residues 55-80). Considering the absence of functional hybrid enzymes in that region, the result could indicate a structural inflexibility of that particular region.

Thirty-one colonies, expressing functional hybrid enzymes, were picked and analyzed by PCR and DNA sequencing. All constructs except one were exactly aligned fusions. Crossovers between the parental gene fragments occurred within regions of different levels of homology. Sequence analysis identified fourteen distinct DNA fusion constructs, four of which were previously unknown. No mutations were identified in the gene fusions created using primer extension for nucleotide analog incorporation. In contrast, DNA sequence analysis of ten functional hybrids created using nucleotide analog incorporation by PCR amplification showed four point mutations in three of the sequences. Two of the mutations were silent (E44, R168) and the other two occurred in the same construct (PurN 1-110/GAR 111-203; A145T/K157R).

In the 31 sequences analyzed, the entire range of functional crossovers from amino acid residue position 80 to 144 is represented and evenly distributed in the library. The frequency of functional hybrids per library size is similar to other embodiments of the present invention.

While the foregoing has been set forth in considerable detail, the examples are presented for elucidation and not for limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein. Accordingly, all such variances should be viewed as being within the scope of the present invention as set forth in the claims below.

What is claimed:

1. A method of making a plurality of incrementally truncated hybrid nucleic acids comprising the steps of:
   a) serially removing nucleotides from one or both termini of a first and a second parent nucleic acid to form truncated first and second parent nucleic acids whose length decreases incrementally over time;
   b) stopping said serial nucleotide removal at a plurality of different times to form a plurality of incrementally truncated first and second parent nucleic acids;
   c) linking separate incrementally truncated first parent nucleic acids to separate incrementally truncated second parent nucleic acids to form a plurality of incrementally truncated hybrid nucleic acids.

2. The method of claim 1 further comprising the step of transforming said plurality of incrementally truncated hybrid nucleic acids into a plurality of hosts to form a plurality of transformed incrementally truncated hybrid nucleic acids.

3. The method of claim 1 wherein said parent nucleic acids each comprise a library of nucleic acids.

4. A method of making a plurality of first variant incrementally truncated hybrid nucleic acids comprising the steps of:
 a) providing a first and second parent nucleic acid;
 b) serially removing nucleotides from one or both termini of said first and second parent nucleic acids to form truncated first and second parent nucleic acids whose length decreases incrementally over time;
 c) stopping said serial nucleotide removal at a plurality of different times to form a plurality of incrementally truncated first and second parent nucleic acids;
 d) linking separate incrementally truncated first parent nucleic acids to separate incrementally truncated second parent nucleic acids to form a plurality of first variant incrementally truncated hybrid nucleic acids, wherein said incrementally truncated first parent nucleic acids form the N-terminal coding sequence of each of said first variant incrementally truncated hybrid genes.

5. The method of claim 4 further comprising the step of transforming the first variant incrementally truncated hybrid nucleic acids into a plurality of hosts to form a plurality of transformed first variant incrementally truncated hybrid nucleic acids.

6. The method of claim 4 wherein said parent nucleic acids comprise a library of nucleic acids.

7. A method of making a plurality of second variant incrementally truncated hybrid nucleic acids comprising the steps of:
 a) providing a first and second parent nucleic acid;
 b) serially removing nucleotides from one or both termini of said first and second parent nucleic acids to form truncated first and second parent nucleic acids whose length decreases incrementally over time;
 c) stopping said serial nucleotide removal at a plurality of different times to form a plurality of incrementally truncated first and second parent nucleic acids;
 d) linking separate incrementally truncated first parent nucleic acids to separate incrementally truncated second parent nucleic acids to form a plurality of second variant incrementally truncated hybrid nucleic acids, wherein said incrementally truncated second parent nucleic acids form the N-terminal coding sequence of each of said second variant incrementally truncated hybrid genes.

8. The method of claim 7 further comprising the step of transforming the second variant incrementally truncated hybrid nucleic acids into a plurality of hosts to form a plurality of transformed first variant incrementally truncated hybrid nucleic acids.

9. The method of claim 7 wherein said parent nucleic acids comprise a library of nucleic acids.

\* \* \* \* \*

SEQUENCE LISTING

<160> NUMBER OF SEQ ID NOS: 13

<210> SEQ ID NO 1
<211> LENGTH: 33
<212> TYPE: DNA
<213> ORGANISM: Escherichia coli

<400> SEQUENCE: 1
ttaggccgtc tagagcgtca ggcaggcgaa ccg     33

<210> SEQ ID NO 2
<211> LENGTH: 32
<212> TYPE: DNA
<213> ORGANISM: Escherichia coli -continued

<400> SEQUENCE: 2
gcggaaaatc tagactggtg cgcaaaatac cg                                    32

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Probe for
      determining the location of the XBaI site.

<400> SEQUENCE: 3
gatatacata tgaatattgt ggtgcttatt tcc                                   33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Primers for
      amplification of the linearized pDIM-PGX.

<400> SEQUENCE: 4
tccggagctt ctagatatcg gatccttagt cc                                    32

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primers for
      amplification of the linearized pDIM-PGX.

<400> SEQUENCE: 5
aggcctctgc agcgctcgag atatcag                                          27

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Restriction
      endonuclease Ndel.

<400> SEQUENCE: 6
aaggagacag tccatatg                                                    18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Restriction
      endonuclease BamHl, EcoRV and Bg/ll.

<400> SEQUENCE: 7
ggatccgata tcagatct                                                    18

<210> SEQ ID NO 8
<211> LENGTH: 9
<212> TYPE: DNA
<213> ORGANISM: Artificial Sequence
<220> FEATURE:
<223> OTHER INFORMATION: Description of Artificial Sequence: Restriction
      endonuclease Spel.

```
<400> SEQUENCE: 8 actagtgct                                                               9

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Restriction
      endonuclease Sacl, Xhol and Bg/ll.

<400> SEQUENCE: 9
gagctcatcg actcgagaca ctatagctaa ctaagatct                              39

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Restriction
      endonuclease Spel.

<400> SEQUENCE: 10
ggaactagta tt                                                          12

<210> SEQ ID NO 11
<211> LENGTH: 6
<212> TYPE: DNA
<213> ORGANISM: Artificial Sequence
<220> FEATURE:
<223> OTHER INFORMATION: Description of Artificial Sequence: Restriction
      endonuclease Nsil.

<400> SEQUENCE: 11 atgcat                                                                  6

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Restriction
      endonuclease BamHi, Xbal, Pstl, Xhol and Bg/ll

<400> SEQUENCE: 12
ggatccgata tctagaagct tactgcagcg ctcgagatat cagatct                    47

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Restriction
      endonuclease Spel

<400> SEQUENCE: 13
actagtgcta cc                                                          12
```